US009733260B2

(12) United States Patent
Michaelsen et al.

(10) Patent No.: US 9,733,260 B2

(45) Date of Patent: Aug. 15, 2017

(54) BIOCHEMICAL MARKERS FOR NEURODEGENERATIVE CONDITIONS

(75) Inventors: Natasha Barascuk Michaelsen, Kobenhavn S (DK); Morten Karsdal, Kobenhavn O (DK); Kim Henriksen, Hillerod (DK)

(73) Assignee: Nordic Biosciences A/S, Herlev (DK)

( * ) Notice: Subject to any disclaimer, the term of this patent is extended or adjusted under 35 U.S.C. 154(b) by 0 days.

(21) Appl. No.: 14/130,927

(22) PCT Filed: Jul. 4, 2012

(86) PCT No.: PCT/EP2012/062965

§ 371 (c)(1),
(2), (4) Date: May 17, 2014

(87) PCT Pub. No.: WO2013/004717

PCT Pub. Date: Jan. 10, 2013

(65) Prior Publication Data

US 2015/0064726 A1 Mar. 5, 2015

(30) Foreign Application Priority Data

Jul. 4, 2011 (GB) .................................... 1111361.0

(51) Int. Cl.

| | |
|---|---|
| ***G01N 33/68*** | (2006.01) |
| ***C12Q 1/37*** | (2006.01) |
| ***C07K 16/18*** | (2006.01) |
| ***C07K 14/47*** | (2006.01) |

(52) U.S. Cl.

CPC ...... *G01N 33/6896* (2013.01); *C07K 14/4711* (2013.01); *C07K 16/18* (2013.01); *C12Q 1/37* (2013.01); *C07K 2317/32* (2013.01); *C07K 2317/33* (2013.01); *C07K 2317/34* (2013.01); *G01N 2333/47* (2013.01); *G01N 2333/96486* (2013.01); *G01N 2800/2821* (2013.01); *G01N 2800/56* (2013.01)

(58) Field of Classification Search

None

See application file for complete search history.

(56) References Cited

U.S. PATENT DOCUMENTS

2008/0050383 A1* 2/2008 Sigurdsson .......... A61K 9/0019 424/141.1
2010/0316564 A1* 12/2010 Sigurdsson ........ A61K 39/0005 424/1.49

FOREIGN PATENT DOCUMENTS

| | | | |
|---|---|---|---|
| WO | 94/13795 | A1 | 6/1994 |
| WO | 01/55725 | A2 | 8/2001 |
| WO | 2010/021755 | A2 | 2/2010 |
| WO | 2011/032155 | A2 | 3/2011 |

OTHER PUBLICATIONS

Paul 2013 "Fundamental Immunology" 7th edition, chapter 7 (p. 199 only).*

US Court of Appeals for the Federal Circuit 2014 "In Re BRCA1 and BRCA2-based hereditary cancer test patent litigation".*

US Court of Appeals for the Federal Circuit 2015 "Ariosa Diagnostics/DNA diagnostics center v. Sequenom/ISIS innovaton".*

Garg, S et al. (2011) Cleavage of Tau by calpain in Alzheimers disease: the quest for the toxic 17 kD fragment. Neurobiology of Aging. vol. 32: pp. 1-14; entire document.

David, DC et al. (2002) Proteasomal degradation of tau protein. J. Neurochem. vol. 83: pp. 176-185; entire document.

Arai, T et al. (2005) Proteolysis of non-phosphorylated and phosphorylated tau by thrombin. J. Biol. Chem. vol. 280: pp. 5145-5153; entire document.

Arriagada, PV et al. (1992) Neurofibrillary tangles but not senile plaques parallel duration and severity of Alzheimer's disease. Neurology. vol. 42: pp. 631-639; entire document.

Barascuk, N et al. (2010) A novel assay for extracellular matrix remodeling associated with liver fibrosis: An enzyme-linked immunosorbent assay (ELISA) for a MMP-9 proteolytically revealed neo-epitope of type III collagen. Clin. Biochem. vol. 43: pp. 899-904; entire document.

Bay-Jensen, AC et al. (2011) Enzyme-linked immunosorbent assay (ELISAs) for metalloproteinase derived type II collagen neoepitope, CIIM--increased serum CIIM in subjects with severe radiographic osteoarthritis. Clin. Biochem. vol. 44: pp. 423-429; entire document.

Cummings, JL. (2011) Biomarkers in Alzheimer's disease drug development. Alzheimer's & Dementia. vol. 7: e13-e44; entire document.

De Calignon, A et al. (2009) Tangle-bearing neurons survive despite disruption of membrane integrity in a mouse model of tauopathy. J. Neuropathol. Exp. Neurol. vol. 68: pp. 757-761; entire document.

De Strooper, B. (2010) Proteases and proteolysis in Alzheimer disease: a multifactorial view on the disease process. Physiol. Rev. vol. 90: pp. 465-494; entire document.

De Strooper, B. et al. (2000) Proteolytic processing and cell biological functions of the amyloid precursor protein. J. Cell Sci. vol. 113: pp. 1857-1870; entire document.

Fillit, H et al. (1995) Disorders of the extracellular matrix and the pathogenesis of senile dementia of the Alzheimer's type. Lab. Invest. vol. 72: pp. 249-253; entire document.

Forstl, H (1999) Clinical features of Alzheimer's disease. Eur. Arch. Psychiatry Clin. Neurosci. vol. 249: pp. 288-290; entire document.

Gamblin, TC et al. (2003) Caspase cleavage of tau: linking amyloid and neurofibrillary tangles in Alzheimer's disease. Proc. Natl. Acad. Sci. USA. vol. 100: pp. 10032-10037; entire document.

(Continued)

*Primary Examiner* — Adam M Weidner

(74) *Attorney, Agent, or Firm* — Benjamin Aaron Adler

(57) ABSTRACT

Provided herein is a method of bioassay for the quantification of peptide fragments relevant to neurodegenerative conditions. The method comprises cleaving a Tau protein by a secretase, such as ADAM10, to form a neo-epitope. The method comprises contacting a blood derived sample with an antibody specific for the neo-epitope and determining the level of binding of the antibody to peptide fragments comprising the neo-epitope in the sample. Neo-epitope containing peptide levels are found to be inversely correlated to cognitive function.

8 Claims, 6 Drawing Sheets

(56) References Cited

OTHER PUBLICATIONS

Garcia-Sierra, F et al. (2008) Truncation of tau protein and its pathological significance in Alzheimer's disease. J. Alzheimer's Disease. vol. 14: pp. 401-409; entire document.
Gefter, ML (1977) A simple method for polyethylene glycol-promoted hybridization of mouse myeloma cells. Somatic Cell Genetics. vol. 3: pp. 231-236; entire document.
Goedert, M et al. (1989) Multiple isoforms of human microtubule-associated protein tau: sequences and localization in neurofibrillary tangles of Alzheimer's disease. Neuron. vol. 3: pp. 519-526; entire document.
Gomez-Isla, T et al. (1997) Neuronal loss correlates with but exceeds neurofibrillary tangles in Alzheimer's disease. Ann. Neurol. vol. 41: pp. 17-24; entire document.
Haass, C et al. (2007) Soluble protein oligomers in neurodegeneration: lessons from the Alzheimer's amyloid beta-peptide. Nat. Rev. Mol. Cell Biol. vol. 8: pp. 101-112; entire document.
Hanger, DP et al. (2010) Tau cleavage and tau aggregation in neurodegenerative disease. Biochem. Soc. Trans. vol. 38: pp. 1016-1020; entire document.
Henriksen, K et al. (2004) Characterization of osteoclasts from patients harboring a G215R mutation in ClC-7 causing autosomal dominant osteopetrosis type II. Am. J. Pathol. vol. 164: pp. 1537-1545; entire document.
Hoglund, K et al. (2008) Prediction of Alzheimer's disease using a cerebrospinal fluid pattern of C-terminally truncated beta-amyloid peptides. Neurodegener. Dis. vol. 5: pp. 268-276; entire document.
Jin, S et al. (2010) Evidence for dimeric BACE-mediated APP processing. Biochem. Biophys. Res. Commun. vol. 393: pp. 21-27; entire document.
Kim, B et al. (2009) Increased tau phosphorylation and cleavage in mouse models of type 1 and type 2 diabetes. Endocrinology vol. 150: pp. 5294-5301; entire document.
McKhann, G et al. (1984) Clinical diagnosis of Alzheimer's disease: report of the NINCDS-ADRDA Work Group under the auspices of Department of Health and Human Services Task Force on Alzheimer's Disease. Neurology. vol. 34: pp. 939-944; entire document.
Molsa, PK et al. (1986) Survival and cause of death in Alzheimer's disease and multi-infarct dementia. Acta Neurol. Scand. vol. 74: pp. 103-107; entire document.
Park, SY et al. (2007) Caspase-3- and calpain-mediated tau cleavage are differentially prevented by estrogen and testosterone in beta-amyloid-treated hippocampal neurons. Neuroscience vol. 144: pp. 119-127; entire document.
Polvikoski, T et al. (1995) Apolipoprotein E, dementia, and cortical deposition of beta-amyloid protein. N. Engl. J. Med. vol. 333: pp. 1242-1247; entire document.
Rametti, A et al. (2004) Linking alterations in tau phosphorylation and cleavage during neuronal apoptosis. J. Biol. Chem. vol. 279: pp. 54518-54528; entire document.
Reifert, J et al. (2011) Amyloid beta-mediated cell death of cultured hippocampal neurons reveals extensive tau fragmentation without increased full-length tau phosphorylation. J. Biol. Chem. vol. 286: pp. 20797-20811; entire document.
Schroeter, ML et al. (2009) Neural correlates of Alzheimer's disease and mild cognitive impairment: a systematic and quantitative meta-analysis involving 1351 patients. Neuroimage. vol. 47: pp. 1196-1206; entire document.
Takeda, S et al. (2010) Plasma beta-amyloid as potential biomarker of Alzheimer disease: possibility of diagnostic tool for Alzheimer disease. Mol. Biosyst. vol. 6: pp. 1760-1766; entire document.
Vassar, R et al. (2011) The beta-secretase enzyme BACE1 as a therapeutic target for Alzheimer's disease. Alzheimers. Res. Ther. vol. 3:20; entire document.
Vincent, B et al. (2011) alpha-Secretase in Alzheimer's disease and beyond: mechanistic, regulation and function in the shedding of membrane proteins. Curr. Alzheimer Res. vol. 9: pp. 140-156; entire document.
Waldemar, G et al. (2007) Recommendations for the diagnosis and management of Alzheimer's disease and other disorders associated with dementia: EFNS guideline. Eur. J. Neurol. vol. 14: e1-e26; entire document.
Zetterberg, H. (2008) Biomarkers reflecting different facets of Alzheimer's disease. Eur. J. Neurol. vol. 15: pp. 1143-1144; entire document.
Zetterberg, H et al. (2008) Elevated cerebrospinal fluid BACE1 activity in incipient Alzheimer disease. Arch. Neurol. vol. 65: pp. 1102-1107; entire document.
Zhang, S et al. (2010) Rapamycin promotes beta-amyloid production via ADAM-10 inhibition. Biochem. Biophys. Res. Commun. vol. 398: pp. 337-341; entire document.

* cited by examiner

SEQUENCE LISTING

```
<160> NUMBER OF SEQ ID NOS: 248

<210> SEQ ID NO 1
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 1

Ala Ala Pro Pro Gly Gln Lys Gly Gln Ala Asn
1               5                   10


<210> SEQ ID NO 2
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 2

Ala Ala Pro Pro Gly Gln Lys Gly Gln Ala Asn Ala Thr
1               5                   10


<210> SEQ ID NO 3
<211> LENGTH: 8
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 3

Ala Pro Val Pro Met Pro Asp Leu
1               5


<210> SEQ ID NO 4
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment
```

<400> SEQUENCE: 4

Ala Pro Val Pro Met Pro Asp Leu Lys
1 5

<210> SEQ ID NO 5
<211> LENGTH: 9
<212> TYPE: PRT
<213> ORGANISM: Homo sapiens
<220> FEATURE:
<221> NAME/KEY: MOD_RES
<222> LOCATION: 5
<223> OTHER INFORMATION: Oxidised Methionine
<220> FEATURE:
<221> NAME/KEY: PEPTIDE
<223> OTHER INFORMATION: Tau protein cleavage fragment

<400> SEQUENCE: 5

Ala Pro Val Pro Met Pro Asp Leu Lys
1 5

<210> SEQ ID NO 6
<211> LENGTH: 8
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 6

Ala Ser Leu Ala Lys Gln Gly Leu
1 5

<210> SEQ ID NO 7
<211> LENGTH: 16
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 7

Ala Thr Leu Ala Asp Glu Val Ser Ala Ser Leu Ala Lys Gln Gly Leu
1 5 10 15

<210> SEQ ID NO 8
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 8

Ala Thr Arg Ile Pro Ala
1 5

<210> SEQ ID NO 9
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 9

Ala Thr Arg Ile Pro Ala Lys Thr Pro Pro Ala Pro Lys
1 5 10

```
<210> SEQ ID NO 10
<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 10

Ala Thr Arg Ile Pro Ala Lys Thr Pro Pro Ala Pro Lys Thr Pro Pro
1               5                   10                  15

Ser Ser Gly Glu Pro Pro Lys
            20


<210> SEQ ID NO 11
<211> LENGTH: 27
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 11

Ala Thr Arg Ile Pro Ala Lys Thr Pro Pro Ala Pro Lys Thr Pro Pro
1               5                   10                  15

Ser Ser Gly Glu Pro Pro Lys Ser Gly Asp Arg
            20                  25


<210> SEQ ID NO 12
<211> LENGTH: 31
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 12

Ala Thr Arg Ile Pro Ala Lys Thr Pro Pro Ala Pro Lys Thr Pro Pro
1               5                   10                  15

Ser Ser Gly Glu Pro Pro Lys Ser Gly Asp Arg Ser Gly Tyr Ser
            20                  25                  30


<210> SEQ ID NO 13
<211> LENGTH: 8
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 13

Asp Glu Ala Ala Gly His Val Thr
1               5


<210> SEQ ID NO 14
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 14

Asp Arg Lys Asp Gln Gly Gly Tyr Thr
1               5
```

<210> SEQ ID NO 15
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 15

```
Glu Ala Ala Gly His Val Thr Gln Ala Arg Met Val Ser Lys Ser Lys
1               5                   10                  15

Asp
```

<210> SEQ ID NO 16
<211> LENGTH: 30
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 16

```
Glu Ala Ala Gly His Val Thr Gln Ala Arg Met Val Ser Lys Ser Lys
1               5                   10                  15

Asp Gly Thr Gly Ser Asp Asp Lys Lys Ala Lys Gly Ala Asp
            20                  25                  30
```

<210> SEQ ID NO 17
<211> LENGTH: 8
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 17

```
Glu Asp His Ala Gly Thr Tyr Gly
1               5
```

<210> SEQ ID NO 18
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 18

```
Glu Gly Asp Thr Asp Ala Gly Leu Lys
1               5
```

<210> SEQ ID NO 19
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 19

```
Glu Asn Ala Lys Ala Lys Thr Asp His Gly Ala Glu Ile Val Tyr
1               5                   10                  15
```

<210> SEQ ID NO 20
<211> LENGTH: 16

```
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 20

Glu Asn Ala Lys Ala Lys Thr Asp His Gly Ala Glu Ile Val Tyr Lys
1               5                   10                  15


<210> SEQ ID NO 21
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 21

Glu Val Met Glu Asp His Ala Gly Thr Tyr Gly
1               5                   10


<210> SEQ ID NO 22
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 22

Glu Val Met Glu Asp His Ala Gly Thr Tyr Gly Leu Gly Asp Arg Lys
1               5                   10                  15

Asp


<210> SEQ ID NO 23
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment
<220> FEATURE:
<221> NAME/KEY: MOD_RES
<222> LOCATION: 3
<223> OTHER INFORMATION: oxidised methionine

<400> SEQUENCE: 23

Glu Val Met Glu Asp His Ala Gly Thr Tyr Gly Leu Gly Asp Arg Lys
1               5                   10                  15

Asp


<210> SEQ ID NO 24
<211> LENGTH: 30
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 24

Glu Val Met Glu Asp His Ala Gly Thr Tyr Gly Leu Gly Asp Arg Lys
1               5                   10                  15

Asp Gln Gly Gly Tyr Thr Met His Gln Asp Gln Glu Gly Asp
            20                  25                  30
```

<210> SEQ ID NO 25
<211> LENGTH: 8
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 25

Glu Val Ser Ala Ser Leu Ala Lys
1               5

<210> SEQ ID NO 26
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 26

Glu Val Ser Ala Ser Leu Ala Lys Gln Gly Leu
1               5                   10

<210> SEQ ID NO 27
<211> LENGTH: 12
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 27

Gly Ala Ala Pro Pro Gly Gln Lys Gly Gln Ala Asn
1               5                   10

<210> SEQ ID NO 28
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 28

Gly Ala Ala Pro Pro Gly Gln Lys Gly Gln Ala Asn Ala Thr
1               5                   10

<210> SEQ ID NO 29
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 29

Gly Glu Pro Pro Lys Ser Gly Asp Arg Ser Gly Tyr Ser
1               5                   10

<210> SEQ ID NO 30
<211> LENGTH: 20
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 30

Gly Ser Pro Gly Thr Pro Gly Ser Arg Ser Arg Thr Pro Ser Leu Pro
1 5 10 15

Thr Pro Pro Thr
20

<210> SEQ ID NO 31
<211> LENGTH: 18
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 31

Gly Thr Pro Gly Ser Arg Ser Arg Thr Pro Ser Leu Pro Thr Pro Pro
1 5 10 15

Thr Arg

<210> SEQ ID NO 32
<211> LENGTH: 38
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 32

His Gly Ala Glu Ile Val Tyr Lys Ser Pro Val Val Ser Gly Asp Thr
1 5 10 15

Ser Pro Arg His Leu Ser Asn Val Ser Ser Thr Gly Ser Ile Asp Met
20 25 30

Val Asp Ser Pro Gln Leu
35

<210> SEQ ID NO 33
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 33

His Lys Pro Gly Gly Gly Gln Val Glu Val Lys
1 5 10

<210> SEQ ID NO 34
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 34

His Val Pro Gly Gly Gly Asn Lys Lys Ile Glu
1 5 10

<210> SEQ ID NO 35
<211> LENGTH: 12
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 35

His Val Pro Gly Gly Gly Asn Lys Lys Ile Glu Thr
1 5 10

<210> SEQ ID NO 36
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 36

His Val Pro Gly Gly Gly Ser Val Gln
1 5

<210> SEQ ID NO 37
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 37

Ile Pro Ala Lys Thr Pro Pro Ala Pro Lys
1 5 10

<210> SEQ ID NO 38
<211> LENGTH: 24
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 38

Ile Pro Ala Lys Thr Pro Pro Ala Pro Lys Thr Pro Pro Ser Ser Gly
1 5 10 15

Glu Pro Pro Lys Ser Gly Asp Arg
20

<210> SEQ ID NO 39
<211> LENGTH: 28
<212> TYPE: PRT
<213> ORGANISM: Homo sapiens
<220> FEATURE:
<221> NAME/KEY: PEPTIDE
<222> LOCATION: 1..28
<223> OTHER INFORMATION: Tau protein cleavage fragment

<400> SEQUENCE: 39

Ile Pro Ala Lys Thr Pro Pro Ala Pro Lys Thr Pro Pro Ser Ser Gly
1 5 10 15

Glu Pro Pro Lys Ser Gly Asp Arg Ser Gly Tyr Ser
20 25

<210> SEQ ID NO 40
<211> LENGTH: 13
<212> TYPE: PRT
<213> ORGANISM: Homo sapiens
<220> FEATURE:
<221> NAME/KEY: PEPTIDE
<222> LOCATION: 1..13
<223> OTHER INFORMATION: Tau protein cleavage fragment

<400> SEQUENCE: 40

Lys Ala Lys Thr Asp His Gly Ala Glu Ile Val Tyr Lys
1               5                   10

<210> SEQ ID NO 41
<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 41

Lys Ser Lys Asp Gly Thr Gly Ser Asp Asp Lys Lys Ala Lys Gly Ala
1               5                   10                  15

Asp Gly Lys Thr Lys Ile Ala
            20

<210> SEQ ID NO 42
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 42

Lys Ser Pro Val Val Ser Gly Asp Thr Ser Pro Arg His Leu Ser
1               5                   10                  15

<210> SEQ ID NO 43
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 43

Lys Thr Pro Pro Ala Pro Lys Thr Pro Pro Ser Ser Gly Glu Pro Pro
1               5                   10                  15

Lys

<210> SEQ ID NO 44
<211> LENGTH: 21
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 44

Lys Thr Pro Pro Ala Pro Lys Thr Pro Pro Ser Ser Gly Glu Pro Pro
1               5                   10                  15

Lys Ser Gly Asp Arg
            20

<210> SEQ ID NO 45
<211> LENGTH: 25
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 45

```
Lys Thr Pro Pro Ala Pro Lys Thr Pro Pro Ser Ser Gly Glu Pro Pro
1               5                   10                  15

Lys Ser Gly Asp Arg Ser Gly Tyr Ser
            20                  25


<210> SEQ ID NO 46
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 46

Leu Ala Lys Gln Gly Leu
1               5


<210> SEQ ID NO 47
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 47

Leu Ala Thr Leu Ala Asp Glu Val Ser Ala Ser Leu Ala Lys Gln Gly
1               5                   10                  15

Leu


<210> SEQ ID NO 48
<211> LENGTH: 31
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 48

Leu Lys Asn Val Lys Ser Lys Ile Gly Ser Thr Glu Asn Leu Lys His
1               5                   10                  15

Gln Pro Gly Gly Gly Lys Val Gln Ile Ile Asn Lys Lys Leu Asp
            20                  25                  30


<210> SEQ ID NO 49
<211> LENGTH: 38
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 49

Leu Lys Asn Val Lys Ser Lys Ile Gly Ser Thr Glu Asn Leu Lys His
1               5                   10                  15

Gln Pro Gly Gly Gly Lys Val Gln Ile Ile Asn Lys Lys Leu Asp Leu
            20                  25                  30

Ser Asn Val Gln Ser Lys
        35


<210> SEQ ID NO 50
<211> LENGTH: 7
<212> TYPE: PRT
<213> ORGANISM: Homo sapiens
```

<220> FEATURE:
<221> NAME/KEY: PEPTIDE
<223> OTHER INFORMATION: Tau protein cleavage fragment

<400> SEQUENCE: 50

Leu Pro Thr Pro Pro Thr Arg
1 5

<210> SEQ ID NO 51
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 51

Leu Pro Thr Pro Pro Thr Arg Glu Pro Lys Lys Val Ala
1 5 10

<210> SEQ ID NO 52
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 52

Leu Pro Thr Pro Pro Thr Arg Glu Pro Lys Lys Val Ala Val Val
1 5 10 15

<210> SEQ ID NO 53
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 53

Met His Gln Asp Gln Glu Gly Asp Thr Asp Ala Gly Leu Lys
1 5 10

<210> SEQ ID NO 54
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment
<220> FEATURE:
<221> NAME/KEY: MOD_RES
<222> LOCATION: 1
<223> OTHER INFORMATION: oxidised methionine

<400> SEQUENCE: 54

Met His Gln Asp Gln Glu Gly Asp Thr Asp Ala Gly Leu Lys
1 5 10

<210> SEQ ID NO 55
<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 55

```
Met Val Asp Ser Pro Gln Leu Ala Thr Leu Ala Asp Glu Val Ser Ala
1               5                   10                  15

Ser Leu Ala Lys Gln Gly Leu
            20


<210> SEQ ID NO 56
<211> LENGTH: 32
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 56

Asn Ala Thr Arg Ile Pro Ala Lys Thr Pro Pro Ala Pro Lys Thr Pro
1               5                   10                  15

Pro Ser Ser Gly Glu Pro Pro Lys Ser Gly Asp Arg Ser Gly Tyr Ser
            20                  25                  30


<210> SEQ ID NO 57
<211> LENGTH: 12
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 57

Asn Ile His His Lys Pro Gly Gly Gly Gln Val Glu
1               5                   10


<210> SEQ ID NO 58
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 58

Asn Ile His His Lys Pro Gly Gly Gly Gln Val Glu Val Lys
1               5                   10


<210> SEQ ID NO 59
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 59

Pro Gly Ser Pro Gly Thr Pro Gly Ser Arg Ser Arg Thr Pro Ser
1               5                   10                  15


<210> SEQ ID NO 60
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 60

Pro Met Pro Asp Leu Lys
1               5
```

<210> SEQ ID NO 61
<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 61

```
Pro Pro Ala Pro Lys Thr Pro Pro Ser Ser Gly Glu Pro Pro Lys Ser
1               5                   10                  15

Gly Asp Arg Ser Gly Tyr Ser
            20
```

<210> SEQ ID NO 62
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 62

```
Pro Pro Lys Ser Gly Asp Arg Ser Gly Tyr Ser
1               5                   10
```

<210> SEQ ID NO 63
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 63

```
Pro Pro Thr Arg Glu Pro Lys Lys Val Ala
1               5                   10
```

<210> SEQ ID NO 64
<211> LENGTH: 16
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 64

```
Pro Ser Ser Gly Glu Pro Pro Lys Ser Gly Asp Arg Ser Gly Tyr Ser
1               5                   10                  15
```

<210> SEQ ID NO 65
<211> LENGTH: 8
<212> TYPE: PRT
<213> ORGANISM: Homo sapiens
<220> FEATURE:
<221> NAME/KEY: PEPTIDE
<222> LOCATION: 1..8
<223> OTHER INFORMATION: Tau protein cleavage fragment

<400> SEQUENCE: 65

```
Pro Val Pro Met Pro Asp Leu Lys
1               5
```

<210> SEQ ID NO 66
<211> LENGTH: 8
<212> TYPE: PRT

<213> ORGANISM: Homo sapiens
<220> FEATURE:
<221> NAME/KEY: PEPTIDE
<223> OTHER INFORMATION: Tau protein cleavage fragment
<220> FEATURE:
<221> NAME/KEY: MOD_RES
<222> LOCATION: 4
<223> OTHER INFORMATION: oxidised methionine

<400> SEQUENCE: 66

Pro Val Pro Met Pro Asp Leu Lys
1 5

<210> SEQ ID NO 67
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 67

Gln Ala Arg Met Val Ser
1 5

<210> SEQ ID NO 68
<211> LENGTH: 18
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 68

Gln Leu Ala Thr Leu Ala Asp Glu Val Ser Ala Ser Leu Ala Lys Gln
1 5 10 15

Gly Leu

<210> SEQ ID NO 69
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 69

Gln Thr Ala Pro Val Pro Met Pro Asp Leu
1 5 10

<210> SEQ ID NO 70
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 70

Gln Thr Ala Pro Val Pro Met Pro Asp Leu Lys
1 5 10

<210> SEQ ID NO 71
<211> LENGTH: 11
<212> TYPE: PRT
<213> ORGANISM: Homo sapiens
<220> FEATURE:
<221> NAME/KEY: PEPTIDE -continued
<223> OTHER INFORMATION: Tau protein cleavage fragment
<220> FEATURE:
<221> NAME/KEY: MOD_RES
<222> LOCATION: 7
<223> OTHER INFORMATION: oxidised methionine

<400> SEQUENCE: 71

Gln Thr Ala Pro Val Pro Met Pro Asp Leu Lys
1 5 10

<210> SEQ ID NO 72
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 72

Arg Glu Asn Ala Lys Ala Lys Thr Asp His Gly Ala Glu Ile Val Tyr
1 5 10 15

Lys

<210> SEQ ID NO 73
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 73

Arg Ile Pro Ala Lys Thr Pro Pro Ala Pro Lys
1 5 10

<210> SEQ ID NO 74
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 74

Arg Ile Pro Ala Lys Thr Pro Pro Ala Pro Lys Thr Pro Pro Ser
1 5 10 15

<210> SEQ ID NO 75
<211> LENGTH: 21
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 75

Arg Ile Pro Ala Lys Thr Pro Pro Ala Pro Lys Thr Pro Pro Ser Ser
1 5 10 15

Gly Glu Pro Pro Lys
20

<210> SEQ ID NO 76
<211> LENGTH: 25
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 76

```
Arg Ile Pro Ala Lys Thr Pro Pro Ala Pro Lys Thr Pro Pro Ser Ser
1               5                   10                  15

Gly Glu Pro Pro Lys Ser Gly Asp Arg
            20                  25
```

<210> SEQ ID NO 77
<211> LENGTH: 29
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 77

```
Arg Ile Pro Ala Lys Thr Pro Pro Ala Pro Lys Thr Pro Pro Ser Ser
1               5                   10                  15

Gly Glu Pro Pro Lys Ser Gly Asp Arg Ser Gly Tyr Ser
            20                  25
```

<210> SEQ ID NO 78
<211> LENGTH: 12
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 78

```
Arg Lys Asp Gln Gly Gly Tyr Thr Met His Gln Asp
1               5                   10
```

<210> SEQ ID NO 79
<211> LENGTH: 18
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 79

```
Arg Lys Asp Gln Gly Gly Tyr Thr Met His Gln Asp Gln Glu Gly Asp
1               5                   10                  15

Thr Asp
```

<210> SEQ ID NO 80
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 80

```
Arg Thr Pro Pro Lys Ser Pro Ser Ser Ala
1               5                   10
```

<210> SEQ ID NO 81
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 81

Arg Thr Pro Pro Lys Ser Pro Ser Ser Ala Lys Ser Arg Leu
1 5 10

<210> SEQ ID NO 82
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 82

Arg Thr Pro Pro Lys Ser Pro Ser Ser Ala Lys Ser Arg Leu Gln
1 5 10 15

<210> SEQ ID NO 83
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 83

Arg Thr Pro Ser Leu Pro Thr Pro Pro Thr
1 5 10

<210> SEQ ID NO 84
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 84

Arg Thr Pro Ser Leu Pro Thr Pro Pro Thr Arg
1 5 10

<210> SEQ ID NO 85
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 85

Arg Thr Pro Ser Leu Pro Thr Pro Pro Thr Arg Glu Pro Lys
1 5 10

<210> SEQ ID NO 86
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 86

Arg Thr Pro Ser Leu Pro Thr Pro Pro Thr Arg Glu Pro Lys Lys Val
1 5 10 15

Ala

<210> SEQ ID NO 87
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 87

Ser Ala Ser Leu Ala Lys Gln Gly Leu
1 5

<210> SEQ ID NO 88
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 88

Ser Glu Lys Leu Asp Phe
1 5

<210> SEQ ID NO 89
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 89

Ser Gly Asp Thr Ser Pro Arg His Leu Ser
1 5 10

<210> SEQ ID NO 90
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 90

Ser Gly Glu Pro Pro Lys Ser Gly Asp Arg Ser Gly Tyr Ser
1 5 10

<210> SEQ ID NO 91
<211> LENGTH: 7
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 91

Ser Leu Ala Lys Gln Gly Leu
1 5

<210> SEQ ID NO 92
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 92

```
Ser Pro Gly Ser Pro Gly Thr Pro Gly Ser Arg
1               5                   10


<210> SEQ ID NO 93
<211> LENGTH: 12
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 93

Ser Pro Gly Ser Pro Gly Thr Pro Gly Ser Arg Ser
1               5                   10


<210> SEQ ID NO 94
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 94

Ser Pro Gly Ser Pro Gly Thr Pro Gly Ser Arg Ser Arg
1               5                   10


<210> SEQ ID NO 95
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 95

Ser Pro Gly Ser Pro Gly Thr Pro Gly Ser Arg Ser Arg Thr
1               5                   10


<210> SEQ ID NO 96
<211> LENGTH: 16
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 96

Ser Pro Gly Ser Pro Gly Thr Pro Gly Ser Arg Ser Arg Thr Pro Ser
1               5                   10                  15


<210> SEQ ID NO 97
<211> LENGTH: 22
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 97

Ser Pro Gly Ser Pro Gly Thr Pro Gly Ser Arg Ser Arg Thr Pro Ser
1               5                   10                  15

Leu Pro Thr Pro Pro Thr
            20


<210> SEQ ID NO 98
```

<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 98

Ser Pro Gly Ser Pro Gly Thr Pro Gly Ser Arg Ser Arg Thr Pro Ser
1 5 10 15

Leu Pro Thr Pro Pro Thr Arg
20

<210> SEQ ID NO 99
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 99

Ser Pro Gly Thr Pro Gly Ser Arg Ser
1 5

<210> SEQ ID NO 100
<211> LENGTH: 26
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 100

Ser Pro Gly Thr Pro Gly Ser Arg Ser Arg Thr Pro Ser Leu Pro Thr
1 5 10 15

Pro Pro Thr Arg Glu Pro Lys Lys Val Ala
20 25

<210> SEQ ID NO 101
<211> LENGTH: 20
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 101

Ser Pro Gln Leu Ala Thr Leu Ala Asp Glu Val Ser Ala Ser Leu Ala
1 5 10 15

Lys Gln Gly Leu
20

<210> SEQ ID NO 102
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 102

Ser Pro Arg His Leu Ser
1 5

<210> SEQ ID NO 103

<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 103

Ser Pro Ser Ser Ala Lys Ser Arg Leu
1 5

<210> SEQ ID NO 104
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 104

Ser Pro Ser Ser Ala Lys Ser Arg Leu Gln
1 5 10

<210> SEQ ID NO 105
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 105

Ser Pro Val Val Ser Gly Asp Thr Ser Pro Arg His Leu Ser
1 5 10

<210> SEQ ID NO 106
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 106

Ser Arg Ser Arg Thr Pro Ser Leu Pro Thr Pro Pro Thr Arg
1 5 10

<210> SEQ ID NO 107
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 107

Ser Arg Thr Pro Ser Leu Pro Thr Pro Pro Thr
1 5 10

<210> SEQ ID NO 108
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 108

Ser Arg Thr Pro Ser Leu Pro Thr Pro Pro Thr Arg Glu Pro Lys
1 5 10 15

<210> SEQ ID NO 109
<211> LENGTH: 18
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 109

Ser Arg Thr Pro Ser Leu Pro Thr Pro Pro Thr Arg Glu Pro Lys Lys
1 5 10 15

Val Ala

<210> SEQ ID NO 110
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 110

Ser Thr Glu Asn Leu Lys
1 5

<210> SEQ ID NO 111
<211> LENGTH: 9
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 111

Thr Ala Pro Val Pro Met Pro Asp Leu
1 5

<210> SEQ ID NO 112
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 112

Thr Ala Pro Val Pro Met Pro Asp Leu Lys
1 5 10

<210> SEQ ID NO 113
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment
<220> FEATURE:
<221> NAME/KEY: MOD_RES
<222> LOCATION: 6
<223> OTHER INFORMATION: oxidised methionine

<400> SEQUENCE: 113

Thr Ala Pro Val Pro Met Pro Asp Leu Lys
1 5 10

<210> SEQ ID NO 114
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 114

Thr Ala Pro Val Pro Met Pro Asp Leu Lys Asn
1 5 10

<210> SEQ ID NO 115
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 115

Thr Ala Pro Val Pro Met Pro Asp Leu Lys Asn Val Lys
1 5 10

<210> SEQ ID NO 116
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 116

Thr Leu Ala Asp Glu Val Ser Ala Ser Leu Ala Lys Gln Gly Leu
1 5 10 15

<210> SEQ ID NO 117
<211> LENGTH: 6
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 117

Thr Pro Pro Ala Pro Lys
1 5

<210> SEQ ID NO 118
<211> LENGTH: 16
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 118

Thr Pro Pro Ala Pro Lys Thr Pro Pro Ser Ser Gly Glu Pro Pro Lys
1 5 10 15

<210> SEQ ID NO 119
<211> LENGTH: 20
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 119

Thr Pro Pro Ala Pro Lys Thr Pro Pro Ser Ser Gly Glu Pro Pro Lys
1 5 10 15

Ser Gly Asp Arg
20

<210> SEQ ID NO 120
<211> LENGTH: 24
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 120

Thr Pro Pro Ala Pro Lys Thr Pro Pro Ser Ser Gly Glu Pro Pro Lys
1 5 10 15

Ser Gly Asp Arg Ser Gly Tyr Ser
20

<210> SEQ ID NO 121
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 121

Thr Pro Pro Lys Ser Pro Ser Ser Ala Lys
1 5 10

<210> SEQ ID NO 122
<211> LENGTH: 13
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 122

Thr Pro Pro Lys Ser Pro Ser Ser Ala Lys Ser Arg Leu
1 5 10

<210> SEQ ID NO 123
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 123

Thr Pro Pro Lys Ser Pro Ser Ser Ala Lys Ser Arg Leu Gln
1 5 10

<210> SEQ ID NO 124
<211> LENGTH: 14
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 124

Thr Pro Pro Ser Ser Gly Glu Pro Pro Lys Ser Gly Asp Arg 1 5 10

<210> SEQ ID NO 125
<211> LENGTH: 18
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 125

Thr Pro Pro Ser Ser Gly Glu Pro Pro Lys Ser Gly Asp Arg Ser Gly
1 5 10 15

Tyr Ser

<210> SEQ ID NO 126
<211> LENGTH: 11
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 126

Thr Pro Arg Gly Ala Ala Pro Pro Gly Gln Lys
1 5 10

<210> SEQ ID NO 127
<211> LENGTH: 15
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 127

Thr Pro Arg Gly Ala Ala Pro Pro Gly Gln Lys Gly Gln Ala Asn
1 5 10 15

<210> SEQ ID NO 128
<211> LENGTH: 17
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 128

Thr Pro Arg Gly Ala Ala Pro Pro Gly Gln Lys Gly Gln Ala Asn Ala
1 5 10 15

Thr

<210> SEQ ID NO 129
<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 129

Thr Pro Ser Leu Glu Asp Glu Ala Ala Gly His Val Thr Gln Ala Arg
1 5 10 15

Met Val Ser Lys Ser Lys Asp
20

<210> SEQ ID NO 130
<211> LENGTH: 30
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 130

```
Thr Arg Ile Pro Ala Lys Thr Pro Pro Ala Pro Lys Thr Pro Pro Ser
1               5                   10                  15

Ser Gly Glu Pro Pro Lys Ser Gly Asp Arg Ser Gly Tyr Ser
            20                  25                  30
```

<210> SEQ ID NO 131
<211> LENGTH: 16
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 131

```
Thr Ser Pro Arg His Leu Ser Asn Val Ser Ser Thr Gly Ser Ile Asp
1               5                   10                  15
```

<210> SEQ ID NO 132
<211> LENGTH: 23
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 132

```
Thr Ser Pro Arg His Leu Ser Asn Val Ser Ser Thr Gly Ser Ile Asp
1               5                   10                  15

Met Val Asp Ser Pro Gln Leu
            20
```

<210> SEQ ID NO 133
<211> LENGTH: 39
<212> TYPE: PRT
<213> ORGANISM: Homo sapiens
<220> FEATURE:
<221> NAME/KEY: PEPTIDE
<223> OTHER INFORMATION: Tau protein cleavage fragment
<220> FEATURE:
<221> NAME/KEY: MOD_RES
<222> LOCATION: 17
<223> OTHER INFORMATION: oxidised methionine

<400> SEQUENCE: 133

```
Thr Ser Pro Arg His Leu Ser Asn Val Ser Ser Thr Gly Ser Ile Asp
1               5                   10                  15

Met Val Asp Ser Pro Gln Leu Ala Thr Leu Ala Asp Glu Val Ser Ala
            20                  25                  30

Ser Leu Ala Lys Gln Gly Leu
        35
```

<210> SEQ ID NO 134
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 134

Val Pro Gly Gly Gly Asn Lys Lys Ile Glu
1 5 10

<210> SEQ ID NO 135
<211> LENGTH: 10
<212> TYPE: PRT
<213> ORGANISM: Homo sapiens
<220> FEATURE:
<221> NAME/KEY: PEPTIDE
<223> OTHER INFORMATION: Tau protein cleavage fragment

<400> SEQUENCE: 135

Val Ser Ala Ser Leu Ala Lys Gln Gly Leu
1 5 10

<210> SEQ ID NO 136
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 136

Ala Ala Pro Pro Gly Gln
1 5

<210> SEQ ID NO 137
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 137

Ala Pro Val Pro Met Pro
1 5

<210> SEQ ID NO 138
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment
<220> FEATURE:
<221> NAME/KEY: MOD_RES
<222> LOCATION: 5
<223> OTHER INFORMATION: oxidised methionine

<400> SEQUENCE: 138

Ala Pro Val Pro Met Pro
1 5

<210> SEQ ID NO 139
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 139

Ala Ser Leu Ala Lys Gln
1 5

<210> SEQ ID NO 140
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 140

Ala Thr Leu Ala Asp Glu
1 5

<210> SEQ ID NO 141
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 141

Asp Glu Ala Ala Gly His
1 5

<210> SEQ ID NO 142
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 142

Asp Arg Lys Asp Gln Gly
1 5

<210> SEQ ID NO 143
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 143

Glu Ala Ala Gly His Val
1 5

<210> SEQ ID NO 144
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 144

Glu Asp His Ala Gly Thr 1 5

<210> SEQ ID NO 145
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 145

Glu Gly Asp Thr Asp Ala
1 5

<210> SEQ ID NO 146
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 146

Glu Asn Ala Lys Ala Lys
1 5

<210> SEQ ID NO 147
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 147

Glu Val Met Glu Asp His
1 5

<210> SEQ ID NO 148
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment
<220> FEATURE:
<221> NAME/KEY: MOD_RES
<222> LOCATION: 3
<223> OTHER INFORMATION: oxidised methionine

<400> SEQUENCE: 148

Glu Val Met Glu Asp His
1 5

<210> SEQ ID NO 149
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 149

Glu Val Ser Ala Ser Leu 1 5

<210> SEQ ID NO 150
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 150

Gly Ala Ala Pro Pro Gly
1 5

<210> SEQ ID NO 151
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 151

Gly Glu Pro Pro Lys Ser
1 5

<210> SEQ ID NO 152
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 152

Gly Ser Pro Gly Thr Pro
1 5

<210> SEQ ID NO 153
<211> LENGTH: 6
<212> TYPE: PRT
<213> ORGANISM: Homo sapiens
<220> FEATURE:
<221> NAME/KEY: PEPTIDE
<223> OTHER INFORMATION: N- or C-terminal sequence of Tau protein cleavage fragment

<400> SEQUENCE: 153

Gly Thr Pro Gly Ser Arg
1 5

<210> SEQ ID NO 154
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 154

His Gly Ala Glu Ile Val
1 5

<210> SEQ ID NO 155

<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 155

His Lys Pro Gly Gly Gly
1               5

<210> SEQ ID NO 156
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 156

Ile Pro Ala Lys Thr Pro
1               5

<210> SEQ ID NO 157
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 157

Lys Ala Lys Thr Asp His
1               5

<210> SEQ ID NO 158
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 158

Lys Ser Lys Asp Gly Thr
1               5

<210> SEQ ID NO 159
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 159

Lys Ser Pro Val Val Ser
1               5

<210> SEQ ID NO 160
<211> LENGTH: 6
<212> TYPE: PRT
<213> ORGANISM: Homo sapiens
<220> FEATURE:

```
<221> NAME/KEY: PEPTIDE
<223> OTHER INFORMATION: N-terminal sequence of Tau protein cleavage
      fragment

<400> SEQUENCE: 160

Lys Thr Pro Pro Ala Pro
1               5


<210> SEQ ID NO 161
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 161

Leu Ala Thr Leu Ala Asp
1               5


<210> SEQ ID NO 162
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 162

Leu Lys Asn Val Lys Ser
1               5


<210> SEQ ID NO 163
<211> LENGTH: 6
<212> TYPE: PRT
<213> ORGANISM: Homo sapiens
<220> FEATURE:
<221> NAME/KEY: PEPTIDE
<223> OTHER INFORMATION: N- or C-terminal sequence of Tau protein
      cleavage fragment

<400> SEQUENCE: 163

Leu Pro Thr Pro Pro Thr
1               5


<210> SEQ ID NO 164
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 164

Met His Gln Asp Gln Glu
1               5


<210> SEQ ID NO 165
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment
<220> FEATURE:
```

<221> NAME/KEY: MOD_RES
<222> LOCATION: 1
<223> OTHER INFORMATION: oxidised methionine

<400> SEQUENCE: 165

Met His Gln Asp Gln Glu
1 5

<210> SEQ ID NO 166
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 166

Met Val Asp Ser Pro Gln
1 5

<210> SEQ ID NO 167
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 167

Asn Ala Thr Arg Ile Pro
1 5

<210> SEQ ID NO 168
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 168

Asn Ile His His Lys Pro
1 5

<210> SEQ ID NO 169
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 169

Pro Gly Ser Pro Gly Thr
1 5

<210> SEQ ID NO 170
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 170

Pro Pro Ala Pro Lys Thr
1 5

<210> SEQ ID NO 171
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 171

Pro Pro Lys Ser Gly Asp
1 5

<210> SEQ ID NO 172
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 172

Pro Pro Thr Arg Glu Pro
1 5

<210> SEQ ID NO 173
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 173

Pro Val Pro Met Pro Asp
1 5

<210> SEQ ID NO 174
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment
<220> FEATURE:
<221> NAME/KEY: MOD_RES
<222> LOCATION: 4
<223> OTHER INFORMATION: oxidised methionine

<400> SEQUENCE: 174

Pro Val Pro Met Pro Asp
1 5

<210> SEQ ID NO 175
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 175

Gln Leu Ala Thr Leu Ala
1               5

<210> SEQ ID NO 176
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 176

Gln Thr Ala Pro Val Pro
1               5

<210> SEQ ID NO 177
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 177

Arg Glu Asn Ala Lys Ala
1               5

<210> SEQ ID NO 178
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 178

Arg Ile Pro Ala Lys Thr
1               5

<210> SEQ ID NO 179
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 179

Arg Lys Asp Gln Gly Gly
1               5

<210> SEQ ID NO 180
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 180

Arg Thr Pro Pro Lys Ser
1               5

<210> SEQ ID NO 181
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 181

Arg Thr Pro Ser Leu Pro
1 5

<210> SEQ ID NO 182
<211> LENGTH: 6
<212> TYPE: PRT
<213> ORGANISM: Homo sapiens
<220> FEATURE:
<221> NAME/KEY: PEPTIDE
<223> OTHER INFORMATION: N- or C-terminal sequence of Tau protein cleavage fragment

<400> SEQUENCE: 182

Ser Ala Ser Leu Ala Lys
1 5

<210> SEQ ID NO 183
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 183

Ser Gly Asp Thr Ser Pro
1 5

<210> SEQ ID NO 184
<211> LENGTH: 6
<212> TYPE: PRT
<213> ORGANISM: Homo sapiens
<220> FEATURE:
<221> NAME/KEY: PEPTIDE
<223> OTHER INFORMATION: N- or C-terminal sequence of Tau protein cleavage fragment

<400> SEQUENCE: 184

Ser Gly Glu Pro Pro Lys
1 5

<210> SEQ ID NO 185
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 185

Ser Leu Ala Lys Gln Gly
1 5

<210> SEQ ID NO 186
<211> LENGTH: 6

<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 186

Ser Pro Gly Ser Pro Gly
1 5

<210> SEQ ID NO 187
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 187

Ser Pro Gln Leu Ala Thr
1 5

<210> SEQ ID NO 188
<211> LENGTH: 6
<212> TYPE: PRT
<213> ORGANISM: Homo sapiens
<220> FEATURE:
<221> NAME/KEY: PEPTIDE
<223> OTHER INFORMATION: N- or C-terminal sequence of Tau protein cleavage fragment

<400> SEQUENCE: 188

Ser Pro Ser Ser Ala Lys
1 5

<210> SEQ ID NO 189
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 189

Ser Pro Val Val Ser Gly
1 5

<210> SEQ ID NO 190
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 190

Ser Arg Ser Arg Thr Pro
1 5

<210> SEQ ID NO 191
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
fragment

<400> SEQUENCE: 191

Ser Arg Thr Pro Ser Leu
1 5

<210> SEQ ID NO 192
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
fragment

<400> SEQUENCE: 192

Thr Ala Pro Val Pro Met
1 5

<210> SEQ ID NO 193
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
fragment
<220> FEATURE:
<221> NAME/KEY: MOD_RES
<222> LOCATION: 6
<223> OTHER INFORMATION: oxidised methionine

<400> SEQUENCE: 193

Thr Ala Pro Val Pro Met
1 5

<210> SEQ ID NO 194
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
fragment

<400> SEQUENCE: 194

Thr Leu Ala Asp Glu Val
1 5

<210> SEQ ID NO 195
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
fragment

<400> SEQUENCE: 195

Thr Pro Pro Lys Ser Pro
1 5

<210> SEQ ID NO 196
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 196

Thr Pro Pro Ser Ser Gly
1               5

<210> SEQ ID NO 197
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 197

Thr Pro Arg Gly Ala Ala
1               5

<210> SEQ ID NO 198
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 198

Thr Pro Ser Leu Glu Asp
1               5

<210> SEQ ID NO 199
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 199

Thr Arg Ile Pro Ala Lys
1               5

<210> SEQ ID NO 200
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 200

Thr Ser Pro Arg His Leu
1               5

<210> SEQ ID NO 201
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage
      fragment

<400> SEQUENCE: 201

Val Pro Gly Gly Gly Asn
1               5

<210> SEQ ID NO 202
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 202

Val Ser Ala Ser Leu Ala
1               5

<210> SEQ ID NO 203
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 203

Ala Ala Gly His Val Thr
1               5

<210> SEQ ID NO 204
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 204

Ala Glu Ile Val Tyr Lys
1               5

<210> SEQ ID NO 205
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 205

Ala Lys Ser Arg Leu Gln
1               5

<210> SEQ ID NO 206
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 206

Ala Pro Pro Gly Gln Lys
1               5

<210> SEQ ID NO 207
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 207

Asp Leu Lys Asn Val Lys
1               5

<210> SEQ ID NO 208
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 208

Asp Gln Gly Gly Tyr Thr
1               5

<210> SEQ ID NO 209
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 209

Asp Arg Ser Gly Tyr Ser
1               5

<210> SEQ ID NO 210
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 210

Glu Pro Lys Lys Val Ala
1               5

<210> SEQ ID NO 211
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 211

Gly Ala Glu Ile Val Tyr
1               5

<210> SEQ ID NO 212
<211> LENGTH: 6
<212> TYPE: PRT

<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 212

Gly Gly Gly Gln Val Glu
1 5

<210> SEQ ID NO 213
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 213

Gly Gly Gly Ser Val Gln
1 5

<210> SEQ ID NO 214
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 214

Gly Lys Thr Lys Ile Ala
1 5

<210> SEQ ID NO 215
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 215

Gly Asn Lys Lys Ile Glu
1 5

<210> SEQ ID NO 216
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 216

Gly Gln Ala Asn Ala Thr
1 5

<210> SEQ ID NO 217
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 217

Gly Gln Val Glu Val Lys
1 5

<210> SEQ ID NO 218
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 218

Gly Ser Arg Ser Arg Thr
1 5

<210> SEQ ID NO 219
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 219

His Ala Gly Thr Tyr Gly
1 5

<210> SEQ ID NO 220
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 220

Ile Asn Lys Lys Leu Asp
1 5

<210> SEQ ID NO 221
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 221

Lys Ala Lys Gly Ala Asp
1 5

<210> SEQ ID NO 222
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 222

Lys Lys Val Ala Val Val
1 5

<210> SEQ ID NO 223
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 223

Lys Ser Pro Ser Ser Ala
1 5

<210> SEQ ID NO 224
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 224

Leu Gly Asp Arg Lys Asp
1 5

<210> SEQ ID NO 225
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 225

Met Pro Asp Leu Lys Asn
1 5

<210> SEQ ID NO 226
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 226

Asn Lys Lys Ile Glu Thr
1 5

<210> SEQ ID NO 227
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 227

Pro Gly Ser Arg Ser Arg
1 5

<210> SEQ ID NO 228
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 228

Pro Lys Ser Gly Asp Arg
1               5

<210> SEQ ID NO 229
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 229

Pro Lys Thr Pro Pro Ser
1               5

<210> SEQ ID NO 230
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment
<220> FEATURE:
<221> NAME/KEY: MOD_RES
<222> LOCATION: 2
<223> OTHER INFORMATION: oxidised methionine

<400> SEQUENCE: 230

Pro Met Pro Asp Leu Lys
1               5

<210> SEQ ID NO 231
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 231

Pro Thr Pro Pro Thr Arg
1               5

<210> SEQ ID NO 232
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 232

Pro Thr Arg Glu Pro Lys
1               5

<210> SEQ ID NO 233
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 233

Gln Asp Gln Glu Gly Asp
1 5

<210> SEQ ID NO 234
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 234

Gln Glu Gly Asp Thr Asp
1 5

<210> SEQ ID NO 235
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 235

Gln Lys Gly Gln Ala Asn
5

<210> SEQ ID NO 236
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 236

Arg Ser Arg Thr Pro Ser
1 5

<210> SEQ ID NO 237
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 237

Ser Ala Lys Ser Arg Leu
1 5

<210> SEQ ID NO 238
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 238

Ser Asn Val Gln Ser Lys
1 5

<210> SEQ ID NO 239
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 239

Ser Thr Gly Ser Ile Asp
1 5

<210> SEQ ID NO 240
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 240

Thr Asp Ala Gly Leu Lys
1 5

<210> SEQ ID NO 241
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 241

Thr Pro Gly Ser Arg Ser
1 5

<210> SEQ ID NO 242
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 242

Val Asp Ser Pro Gln Leu
1 5

<210> SEQ ID NO 243
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 243

Val Pro Met Pro Asp Leu
1 5

<210> SEQ ID NO 244
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 244

Val Ser Lys Ser Lys Asp
1 5

<210> SEQ ID NO 245
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Tau protein cleavage fragment

<400> SEQUENCE: 245

Tyr Thr Met His Gln Asp
1 5

<210> SEQ ID NO 246
<211> LENGTH: 10
<212> TYPE: PRT
<213> ORGANISM: Homo sapiens
<220> FEATURE:
<221> NAME/KEY: PEPTIDE
<223> OTHER INFORMATION: N-terminal sequence of Tau protein cleavage fragment

<400> SEQUENCE: 246

Thr Pro Arg Gly Ala Ala Pro Pro Gly Gln
1 5 10

<210> SEQ ID NO 247
<211> LENGTH: 11
<212> TYPE: PRT
<213> ORGANISM: Artificial sequence
<220> FEATURE:
<221> NAME/KEY: PEPTIDE
<223> OTHER INFORMATION: synthetic de-selection peptide

<400> SEQUENCE: 247

Ala Thr Pro Arg Gly Ala Ala Pro Pro Gly Gln
1 5 10

<210> SEQ ID NO 248
<211> LENGTH: 13
<212> TYPE: PRT
<213> ORGANISM: Artificial sequence
<220> FEATURE:
<221> NAME/KEY: PEPTIDE
<223> OTHER INFORMATION: synthetic immunogenic peptide

<400> SEQUENCE: 248

Thr Pro Arg Gly Ala Ala Pro Pro Gly Gln Gly Gly Cys
1 5 10

BIOCHEMICAL MARKERS FOR NEURODEGENERATIVE CONDITIONS

The present invention relates to the development of biomarkers for neurodegenerative conditions or for neurodegeneration and more particularly to assays for detection of biochemical markers valuable for diagnostic purposes in Alzheimer's disease and prognosis of disease development, including biochemical markers indicative of response to treatment regimens.

Alzheimer's disease (AD), often referred to as Alzheimer's, is a progressive and ultimately fatal neurological condition mainly affecting people above the age of 65 years. Worldwide AD affects an estimated 35.6 million people (2009), and the number is expected to double every 20 years. In the US alone the costs of AD amount to more than $148 billion per year, and that number is in excess of $320 billion worldwide [3], and when comparing the costs related to care for dementia (of which AD is 50-75% of the cases), these clearly exceed the costs related to care for cancer and heart disease, underlining that AD is a severe societal burden both from an individual point-of-view, and from a health care point-of-view. Although the course of Alzheimer's disease is individual, there are common symptoms, of which the earliest often are cognitive, and mistakenly considered to due to increased age or stress [37]. Early symptoms include failing short term memory, and if suspected, behavioural assessments and cognitive tests, and if possible an MR-scan of the brain, are performed to strengthen the diagnosis [37]. As the disease progresses, symptoms include a series of neurological issues, such as confusion, irritability and aggression, language breakdown, long-term memory loss, leading the individuals to become introvert [2]. Finally, bodily functions begin breaking down, ultimately resulting in death, and the mean life expectancy following diagnosis is approximately seven years [2;28].

A major issue in relation to better treating and understanding AD, is that the early development of disease is veiled, and thus AD has often progressed for several years becoming fully apparent leading to diagnosis [13]. Furthermore, in most cases, an individual with the symptoms of AD will generally be diagnosed as a "probable" sufferer of the disease only when other possible causes for the symptoms have been ruled out. Although diagnostic criteria have been standardized through the use of intellectual function testing, it is still generally accepted that AD can only be diagnosed definitively by autopsy [27].

Recent studies have indicated that some progress has been made using biochemical markers as well as imaging techniques; however, these approaches still need further characterization and validation, and are often limited by lack of sensitivity in the early stages of development [24;33;34;38;39].

Currently used treatments offer a small palliative benefit; and treatments with the ability to slow down or prevent progression are a hotly pursued commodity, as illustrated by the fact that more than 500 clinical trials have been conducted for identification of a possible treatment for AD, and as of yet none have clearly identified a treatment possibility [1]. These data, together with the lack of established biomarkers of AD, clearly illustrate the necessity of investment into the development of biomarkers which can reflect more accurately important aspects of AD, such as disease onset, progression and response to therapy.

Assessment of Alzheimer's risk is close to impossible, except in the cases involving the APOE $\epsilon 4$ variant [8]. Furthermore, monitoring efficacy of trial drugs is possible, but often is attached directly to the mode of action of the drug, rather than to the overall pathology of AD [8].

Analysis of brain tissue from AD individuals has highlighted the disturbance of the extracellular matrix remodeling [12], mainly showing two important phenomena, namely the formation of plaques containing beta amyloid (Aβ), as well as the formation of Neurofibrillary Tangles containing a modified version of the Tau protein [10]. Both of these processes are highly relevant for disease progression, and interestingly deposition of Aβ in plaques precedes the actual neuronal damage [30], but is involving in triggering the formation of Neurofibrillary tangles [32], which appears to be the main reason for neuronal cell death [5;18]. APP is an integral membrane protein expressed in many tissues and concentrated in the synapses of neurons. Its primary function is not known, and it is most commonly studied as the precursor molecule of beta amyloid (Aβ), a 39- to 42-amino acid peptide, which when present in the amyloid fibrillar form is the primary component of amyloid plaques [10]. Aβ is produced from two proteolytic cleavages, first by β-secretase (BACE-1) and the second cleavage is performed by the γ-secretase. These sequential biochemical events are essential for Aβ formation [10]. Furthermore, other enzymatic cleavages, such as those by ADAM10 (A Disintegrin And Metalloproteinase 10) and presenilin-1, as well as other types of post-translational modifications of APP, result in modified peptide fragments of which the clinical significance has not yet been completely clarified, although they are expected to related to disease progression [10;11;19;25;40].

Tau proteins are microtubule stabilizing proteins, which are highly abundant in neurons of the central nervous system, whereas they are rare outside the CNS, and Tau is an important component in the formation of Neurofibrillary tangles in AD [10]. Furthermore, mutations in Tau are relevant for a panel of neurodegenerative disorders, referred to a Tauopathies; however, AD is by far the most common disease involving changes in Tau proteins [10;17]. Post-translational modifications, such as phosphorylation and enzymatic cleavage, have been shown to modulate the ability of Tau to stabilize the microtubules leading to formation of Neurofibrillary tangles, as well as potential formation of small toxic protein aggregates, which may contribute to neuronal death and thereby disease progression [10;19]. The MAPT (Microtubule Associated Protein Tau) gene for encoding tau protein is located on chromosome 17q21, containing 16 exons. The major tau protein in the human brain is encoded by 11 exons. Exons 2, 3 and 10 are alternatively spliced, allowing six combinations ($2^-3^-10^-$; $2^+3^-10^-$; $2^+3^+10^-$; $2^-3^-10^+$; $2^+3^-10^+$; $2^+3^+10^+$). Thus, in the human brain, the tau proteins constitute a family of six isoforms with the range from 352-441 amino acids. They differ in either zero, one or two inserts of 29 amino acids at the N-terminal part (exon 2 and 3), and three or four repeat-regions at the C-terminal part exon 10 missing. So, the longest isoform in the CNS has four repeats (R1, R2, R3 and R4) and two inserts (441 amino acids total), while the shortest isoform has three repeats (R1, R3 and R4) and no insert (352 amino acids total) [20]. The MAPT gene has two haplogroups, H1 and H2, in which the gene appears in inverted orientations. Haplogroup H2 is common only in Europe and in people with European ancestry. Haplogroup H1 appears to be associated with increased probability of certain dementias, such as Alzheimer's disease. All of these isoforms are found in neurons; however, it is not clear to what extent the different isoforms play roles in the pathology of Alzheimer's disease [20].

The enzymes involved in Tau processing include caspases, thrombin, as well as other proteases highly relevant for tissue turnover in neurons, such as MMPs [4;10;10;14;15;19;26;29;31]. The present invention is however concerned with a further enzyme group, namely the secretases.

Three types of secretases exist, α, β and γ-secretases [10]. The enzymes referred to as secretases are classically associated with the extracellular cleavage of a protein, which in the context of Alzheimer's mainly has been related to cleavage of Amyloid Precursor Protein (APP) leading to the generation of Amyloid β, which is the major determinant of amyloid plaque formation [10]. These categories are defined by the site in the protein, at which they cleave APP, however, in terms of pathological relevance disturbances in the function of any of the three types of secretase are known to cause Alzheimer's like pathology [10;11;35;36].

The list of enzymes includes:

α-secretases include: ADAM9, 10, 17 (TACE), 19 and BACE2

β-secretases include: BACE1 and 2

γ-secretase complex: Presenilin 1 and/or 2, Nicastrin, Aph-1a, Aph1b and Pen-2.

Due to their described role as secretases the ability of these enzymes to degrade Tau has never been assessed. However, it is well-known that Tau is extensively processed during the progression of Alzheimer's disease [14;15;17;26;29]. The enzymes known to cleave Tau, and hence indicated to be involved in the induction of neuronal death include the caspase family and the calpains, and treatment of Tau with these enzymes leads to the generation of a series of well-described fragments, which are speculated to cause neuronal cell death [10;32].

We have now explored the possibility that secretase mediated cleavage of Tau would lead to the generation of fragments, which could be used as biomarkers of Alzheimer's diseases.

The present invention now provides in a first aspect a method of bioassay for the quantification of peptide fragments comprising a neo-epitope formed by cleavage of a protein by a secretase, said method comprising contacting a sample comprising said peptide fragments with an immunological binding partner having specific binding affinity for a said neo-epitope and determining the level of binding of said immunological binding partner to peptide fragments in said sample, wherein said protein is a Tau protein.

The Tau protein may be from any mammalian, including rodent, e.g. mouse or rat, and also including dog or monkey, but is preferably human.

The neo-epitope is preferably one which is not formed by cleavage of Tau by the caspase family and/or the calpains.

Optionally, said immunological binding partner has specific binding affinity for peptide fragments comprising a C-terminal neo-epitope of a Tau protein. Alternatively, said immunological binding partner has specific binding affinity for peptide fragments comprising an N-terminal neo-epitope of a Tau protein.

The protein may be Tau-A or any other member of the Tau family. The neo-epitope may be common to two or more or all of the Tau proteins.

The neo-epitope may preferably be formed by cleavage of a Tau protein by ADAM10 or BASE-1. It may be formed by more than one secretase.

Said immunological binding partner preferably has specific binding affinity for a peptide fragment which comprises a neo-epitope formed by cleavage of a Tau protein by a protease giving any one of the following partial sequences of human Tau (Table 1):

SEQ ID NO 1
AAPPGQKGQAN

SEQ ID NO 2
AAPPGQKGQANAT

SEQ ID NO 3
APVPMPDL

SEQ ID NO 4
APVPMPDLK

SEQ ID NO 5
APVPMPDLK

SEQ ID NO 6
ASLAKQGL

SEQ ID NO 7
ATLADEVSASLAKQGL

SEQ ID NO 8
ATRIPA

SEQ ID NO 9
ATRIPAKTPPAPK

SEQ ID NO 10
ATRIPAKTPPAPKTPPSSGEPPK

SEQ ID NO 11
ATRIPAKTPPAPKTPPSSGEPPKSGDR

SEQ ID NO 12
ATRIPAKTPPAPKTPPSSGEPPKSGDRSGYS

SEQ ID NO 13
DEAAGHVT

SEQ ID NO 14
DRKDQGGYT

SEQ ID NO 15
EAAGHVTQARMVSKSKD

SEQ ID NO 16
EAAGHVTQARMVSKSKDGTGSDDKKAKGAD

SEQ ID NO 17
EDHAGTYG

SEQ ID NO 18
EGDTDAGLK

SEQ ID NO 19
ENAKAKTDHGAEIVY

SEQ ID NO 20
ENAKAKTDHGAEIVYK

SEQ ID NO 21
EVMEDHAGTYG

SEQ ID NO 22
EVMEDHAGTYGLGDRKD

SEQ ID NO 23
EVMEDHAGTYGLGDRKD

SEQ ID NO 24
EVMEDHAGTYGLGDRKDQGGYTMHQDQEGD

SEQ ID NO 25
EVSASLAK

SEQ ID NO 26
EVSASLAKQGL

SEQ ID NO 27
GAAPPGQKGQAN

-continued

SEQ ID NO 28
GAAPPGQKGQANAT

SEQ ID NO 29
GEPPKSGDRSGYS

SEQ ID NO 30
GSPGTPGSRSRTPSLPTPPT

SEQ ID NO 31
GTPGSRSRTPSLPTPPTR

SEQ ID NO 32
HGAEIVYKSPVVSGDTSPRHLSNVSSTGSIDMVDSPQL

SEQ ID NO 33
HKPGGGQVEVK

SEQ ID NO 34
HVPGGGNKKIE

SEQ ID NO 35
HVPGGGNKKIET

SEQ ID NO 36
HVPGGGSVQ

SEQ ID NO 37
IPAKTPPAPK

SEQ ID NO 38
IPAKTPPAPKTPPSSGEPPKSGDR

SEQ ID NO 39
IPAKTPPAPKTPPSSGEPPKSGDRSGYS

SEQ ID NO 40
KAKTDHGAEIVYK

SEQ ID NO 41
KSKDGTGSDDKKAKGADGKTKIA

SEQ ID NO 42
KSPVVSGDTSPRHLS

SEQ ID NO 43
KTPPAPKTPPSSGEPPK

SEQ ID NO 44
KTPPAPKTPPSSGEPPKSGDR

SEQ ID NO 45
KTPPAPKTPPSSGEPPKSGDRSGYS

SEQ ID NO 46
LAKQGL

SEQ ID NO 47
LATLADEVSASLAKQGL

SEQ ID NO 48
LKNVKSKIGSTENLKHQPGGGKVQIINKKLD

SEQ ID NO 49
LKNVKSKIGSTENLKHQPGGGKVQIINKKLDLSNVQSK

SEQ ID NO 50
LPTPPTR

SEQ ID NO 51
LPTPPTREPKKVA

SEQ ID NO 52
LPTPPTREPKKVAVV

SEQ ID NO 53
MHQDQEGDTDAGLK

SEQ ID NO 54
MHQDQEGDTDAGLK

-continued

SEQ ID NO 55
MVDSPQLATLADEVSASLAKQGL

SEQ ID NO 56
NATRIPAKTPPAPKTPPSSGEPPKSGDRSGYS

SEQ ID NO 57
NIHHKPGGGQVE

SEQ ID NO 58
NIHHKPGGGQVEVK

SEQ ID NO 59
PGSPGTPGSRSRTPS

SEQ ID NO 60
PMPDLK

SEQ ID NO 61
PPAPKTPPSSGEPPKSGDRSGYS

SEQ ID NO 62
PPKSGDRSGYS

SEQ ID NO 63
PPTREPKKVA

SEQ ID NO 64
PSSGEPPKSGDRSGYS

SEQ ID NO 65
PVPMPDLK

SEQ ID NO 66
PVPMPDLK

SEQ ID NO 67
QARMVS

SEQ ID NO 68
QLATLADEVSASLAKQGL

SEQ ID NO 69
QTAPVPMPDL

SEQ ID NO 70
QTAPVPMPDLK

SEQ ID NO 71
QTAPVPMPDLK

SEQ ID NO 72
RENAKAKTDHGAEIVYK

SEQ ID NO 73
RIPAKTPPAPK

SEQ ID NO 74
RIPAKTPPAPKTPPS

SEQ ID NO 75
RIPAKTPPAPKTPPSSGEPPK

SEQ ID NO 76
RIPAKTPPAPKTPPSSGEPPKSGDR

SEQ ID NO 77
RIPAKTPPAPKTPPSSGEPPKSGDRSGYS

SEQ ID NO 78
RKDQGGYTMHQD

SEQ ID NO 79
RKDQGGYTMHQDQEGDTD

SEQ ID NO 80
RTPPKSPSSA

SEQ ID NO 81
RTPPKSPSSAKSRL

-continued

SEQ ID NO 82
RTPPKSPSSAKSRLQ

SEQ ID NO 83
RTPSLPTPPT

SEQ ID NO 84
RTPSLPTPPTR

SEQ ID NO 85
RTPSLPTPPTREPK

SEQ ID NO 86
RTPSLPTPPTREPKKVA

SEQ ID NO 87
SASLAKQGL

SEQ ID NO 88
SEKLDF

SEQ ID NO 89
SGDTSPRHLS

SEQ ID NO 90
SGEPPKSGDRSGYS

SEQ ID NO 91
SLAKQGL

SEQ ID NO 92
SPGSPGTPGSR

SEQ ID NO 93
SPGSPGTPGSRS

SEQ ID NO 94
SPGSPGTPGSRSR

SEQ ID NO 95
SPGSPGTPGSRSRT

SEQ ID NO 96
SPGSPGTPGSRSRTPS

SEQ ID NO 97
SPGSPGTPGSRSRTPSLPTPPT

SEQ ID NO 98
SPGSPGTPGSRSRTPSLPTPPTR

SEQ ID NO 99
SPGTPGSRS

SEQ ID NO 100
SPGTPGSRSRTPSLPTPPTREPKKVA

SEQ ID NO 101
SPQLATLADEVSASLAKQGL

SEQ ID NO 102
SPRHLS

SEQ ID NO 103
SPSSAKSRL

SEQ ID NO 104
SPSSAKSRLQ

SEQ ID NO 105
SPVVSGDTSPRHLS

SEQ ID NO 106
SRSRTPSLPTPPTR

SEQ ID NO 107
SRTPSLPTPPT

SEQ ID NO 108
SRTPSLPTPPTREPK

-continued

SEQ ID NO 109
SRTPSLPTPPTREPKKVA

SEQ ID NO 110
STENLK

SEQ ID NO 111
TAPVPMPDL

SEQ ID NO 112
TAPVPMPDLK

SEQ ID NO 113
TAPVPMPDLK

SEQ ID NO 114
TAPVPMPDLKN

SEQ ID NO 115
TAPVPMPDLKNVK

SEQ ID NO 116
TLADEVSASLAKQGL

SEQ ID NO 117
TPPAPK

SEQ ID NO 118
TPPAPKTPPSSGEPPK

SEQ ID NO 119
TPPAPKTPPSSGEPPKSGDR

SEQ ID NO 120
TPPAPKTPPSSGEPPKSGDRSGYS

SEQ ID NO 121
TPPKSPSSAK

SEQ ID NO 122
TPPKSPSSAKSRL

SEQ ID NO 123
TPPKSPSSAKSRLQ

SEQ ID NO 124
TPPSSGEPPKSGDR

SEQ ID NO 125
TPPSSGEPPKSGDRSGYS

SEQ ID NO 126
TPRGAAPPGQK

SEQ ID NO 127
TPRGAAPPGQKGQAN

SEQ ID NO 128
TPRGAAPPGQKGQANAT

SEQ ID NO 129
TPSLEDEAAGHVTQARMVSKSKD

SEQ ID NO 130
TRIPAKTPPAPKTPPSSGEPPKSGDRSGYS

SEQ ID NO 131
TSPRHLSNVSSTGSID

SEQ ID NO 132
TSPRHLSNVSSTGSIDMVDSPQL

SEQ ID NO 133
TSPRHLSNVSSTGSIDMVDSPQLATLADEVSASLAKQGL

SEQ ID NO 134
VPGGGNKKIE

SEQ ID NO 135
VSASLAKQGL where M indicates an oxidised methionine.

Said immunological binding partner may have specific binding affinity for any of the following sequences at the N terminal of a peptide (Table 2):

| | |
|---|---|
| AAPPGQ | SEQ ID NO 136 |
| APVPMP | SEQ ID NO 137 |
| APVPMP | SEQ ID NO 138 |
| ASLAKQ | SEQ ID NO 139 |
| ATLADE | SEQ ID NO 140 |
| ATRIPA | SEQ ID NO 8 |
| DEAAGH | SEQ ID NO 141 |
| DRKDQG | SEQ ID NO 142 |
| EAAGHV | SEQ ID NO 143 |
| EDHAGT | SEQ ID NO 144 |
| EGDTDA | SEQ ID NO 145 |
| ENAKAK | SEQ ID NO 146 |
| EVMEDH | SEQ ID NO 147 |
| EVMEDH | SEQ ID NO 148 |
| EVSASL | SEQ ID NO 149 |
| GAAPPG | SEQ ID NO 150 |
| GEPPKS | SEQ ID NO 151 |
| GSPGTP | SEQ ID NO 152 |
| GTPGSR | SEQ ID NO 153 |
| HGAEIV | SEQ ID NO 154 |
| HKPGGG | SEQ ID NO 155 |
| IPAKTP | SEQ ID NO 156 |
| KAKTDH | SEQ ID NO 157 |
| KSKDGT | SEQ ID NO 158 |
| KSPVVS | SEQ ID NO 159 |
| KTPPAP | SEQ ID NO 160 |
| LAKQGL | SEQ ID NO 46 |
| LATLAD | SEQ ID NO 161 |
| LKNVKS | SEQ ID NO 162 |
| LPTPPT | SEQ ID NO 163 |
| MHQDQE | SEQ ID NO 164 |
| MHQDQE | SEQ ID NO 165 |
| MVDSPQ | SEQ ID NO 166 |
| NATRIP | SEQ ID NO 167 |
| NIHHKP | SEQ ID NO 168 |
| PGSPGT | SEQ ID NO 169 |
| PMPDLK | SEQ ID NO 60 |
| PPAPKT | SEQ ID NO 170 |

-continued

| | |
|---|---|
| PPKSGD | SEQ ID NO 171 |
| PPTREP | SEQ ID NO 172 |
| PVPMPD | SEQ ID NO 173 |
| PVPMPD | SEQ ID NO 174 |
| QARMVS | SEQ ID NO 67 |
| QLATLA | SEQ ID NO 175 |
| QTAPVP | SEQ ID NO 176 |
| RENAKA | SEQ ID NO 177 |
| RIPAKT | SEQ ID NO 178 |
| RKDQGG | SEQ ID NO 179 |
| RTPPKS | SEQ ID NO 180 |
| RTPSLP | SEQ ID NO 181 |
| SASLAK | SEQ ID NO 182 |
| SEKLDF | SEQ ID NO 88 |
| SGDTSP | SEQ ID NO 183 |
| SGEPPK | SEQ ID NO 184 |
| SLAKQG | SEQ ID NO 185 |
| SPGSPG | SEQ ID NO 186 |
| SPQLAT | SEQ ID NO 187 |
| SPRHLS | SEQ ID NO 102 |
| SPSSAK | SEQ ID NO 188 |
| SPVVSG | SEQ ID NO 189 |
| SRSRTP | SEQ ID NO 190 |
| SRTPSL | SEQ ID NO 191 |
| STENLK | SEQ ID NO 110 |
| TAPVPM | SEQ ID NO 192 |
| TAPVPM | SEQ ID NO 193 |
| TLADEV | SEQ ID NO 194 |
| TPPAPK | SEQ ID NO 117 |
| TPPKSP | SEQ ID NO 195 |
| TPPSSG | SEQ ID NO 196 |
| TPRGAA | SEQ ID NO 197 |
| TPSLED | SEQ ID NO 198 |
| TRIPAK | SEQ ID NO 199 |
| TSPRHL | SEQ ID NO 200 |
| VPGGGN | SEQ ID NO 201 |
| VSASLA | SEQ ID NO 202 |

where M indicates an oxidised methionine;

or with any of the following sequences at the C-terminal of a peptide (Table 3):

| | |
|---|---|
| AAGHVT | SEQ ID NO 203 |
| AEIVYK | SEQ ID NO 204 |
| AKSRLQ | SEQ ID NO 205 |
| APPGQK | SEQ ID NO 206 |
| ATRIPA | SEQ ID NO 8 |
| DLKNVK | SEQ ID NO 207 |
| DQGGYT | SEQ ID NO 208 |
| DRSGYS | SEQ ID NO 209 |
| EPKKVA | SEQ ID NO 210 |
| GAEIVY | SEQ ID NO 211 |
| GGGQVE | SEQ ID NO 212 |
| GGGSVQ | SEQ ID NO 213 |
| GKTKIA | SEQ ID NO 214 |
| GNKKIE | SEQ ID NO 215 |
| GQANAT | SEQ ID NO 216 |
| GQVEVK | SEQ ID NO 217 |
| GSRSRT | SEQ ID NO 218 |
| GTPGSR | SEQ ID NO 153 |
| HAGTYG | SEQ ID NO 219 |
| INKKLD | SEQ ID NO 220 |
| KAKGAD | SEQ ID NO 221 |
| KKVAVV | SEQ ID NO 222 |
| KSPSSA | SEQ ID NO 223 |
| LAKQGL | SEQ ID NO 46 |
| LGDRKD | SEQ ID NO 224 |
| LPTPPT | SEQ ID NO 163 |
| MPDLKN | SEQ ID NO 225 |
| NKKIET | SEQ ID NO 226 |
| PGSRSR | SEQ ID NO 227 |
| PKSGDR | SEQ ID NO 228 |
| PKTPPS | SEQ ID NO 229 |
| PMPDLK | SEQ ID NO 60 |
| PMPDLK | SEQ ID NO 230 |
| PTPPTR | SEQ ID NO 231 |
| PTREPK | SEQ ID NO 232 |
| QARMVS | SEQ ID NO 67 |
| QDQEGD | SEQ ID NO 233 |
| QEGDTD | SEQ ID NO 234 |
| QKGQAN | SEQ ID NO 235 |

-continued

| | |
|---|---|
| RSRTPS | SEQ ID NO 236 |
| SAKSRL | SEQ ID NO 237 |
| SASLAK | SEQ ID NO 182 |
| SEKLDF | SEQ ID NO 88 |
| SGEPPK | SEQ ID NO 184 |
| SNVQSK | SEQ ID NO 238 |
| SPRHLS | SEQ ID NO 102 |
| SPSSAK | SEQ ID NO 188 |
| STENLK | SEQ ID NO 110 |
| STGSID | SEQ ID NO 239 |
| TDAGLK | SEQ ID NO 240 |
| TPGSRS | SEQ ID NO 241 |
| TPPAPK | SEQ ID NO 117 |
| VDSPQL | SEQ ID NO 242 |
| VPMPDL | SEQ ID NO 243 |
| VSKSKD | SEQ ID NO 244 |
| YTMHQD | SEQ ID NO 245 |

where M indicates an oxidised methionine.

Preferably, said immunological binding partner has specific binding affinity for the sequence TPRGAAPPGQ (SEQ ID NO 246) at the N terminal of a peptide.

Said immunological binding partner may be a monoclonal antibody or a fragment of a monoclonal antibody having specific binding affinity.

Said method may be conducted as a competition immunoassay in which said immunological binding partner and a competition agent are incubated in the presence of said sample and the competition agent competes with the peptide fragments in the sample to bind to the immunological binding partner. Said competition agent may be a synthetic peptide or is a purified native peptide formed by cleavage of the protein from which said epitope comes so as to reveal said neo-epitope and in particular may be a peptide comprising the N-terminal sequence TPRGAAPPGQ (SEQ ID NO 246).

The sample may be a sample of mammalian, e.g. mouse, rat, dog or monkey, but especially human cerebrospinal fluid, urine, serum, blood, plasma, or saliva. The sample may be a patient derived sample, said method further comprising comparing the determined level of said binding of said peptide fragments with values characteristic of (a) comparable healthy individuals and/or (b) a pathological neurodegenerative condition, particularly Alzheimer's. The measured level may be compared with a previous measurement obtained from the same patient.

In a further aspect, the invention includes an immunological binding partner against a C-terminal or N-terminal neo-epitope formed by secretase cleavage of a Tau protein. The immunological binding partner may be is specifically immunoreactive with the N-terminal of any one of the amino acid sequences of Table 2 or with the C-terminal of any one of the amino acid sequences of Table 3.

The immunological binding partner may be a monoclonal antibody or a binding fragment thereof. The invention includes a cell line producing such a monoclonal antibody or binding fragment.

In a further aspect, the invention includes a peptide comprising a C-terminal or N-terminal neo-epitope formed by cleavage of a Tau protein by a secretase at a terminal of any one of the partial sequences of a said Tau protein set out in Table 1. Said peptide may be conjugated as a hapten to a carrier for producing an immune response to said peptide, or immobilised to a solid surface or conjugated to a detectable marker for use in an immunoassay.

In a further aspect, the invention provides an isolated nucleic acid molecule coding for a peptide comprising a C-terminal or N-terminal neo-epitope formed by cleavage of a said Tau protein by a secretase in any one of the partial sequences of a said Tau protein set out in Table 1.

In a still further aspect, the invention provides a vector comprising a nucleic acid sequence comprising an expression signal and a coding sequence which codes for the expression of a peptide comprising a C-terminal or N-terminal neo-epitope formed by cleavage of a said Tau protein by a secretase in any one of the partial sequences of a said protein set out in Table 1.

In a still further aspect, the invention provides a host cell transformed with a vector as describe above and expressing a said peptide.

In a still further aspect, the invention provides an immunoassay kit comprising an immunological binding partner as describe and a competition agent which binds said immunological binding partner, and optionally one or more of a wash reagent, a buffer, a stopping reagent, an enzyme label, an enzyme label substrate, calibration standards, an anti-mouse antibody and instructions for conducting an assay using said kit.

The invention will be further explained and illustrated with reference to the accompanying drawings, in which.

Figure 3A:
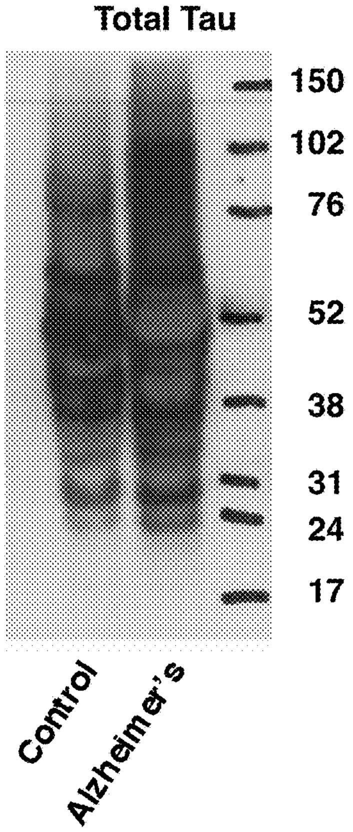
Figure 3B:
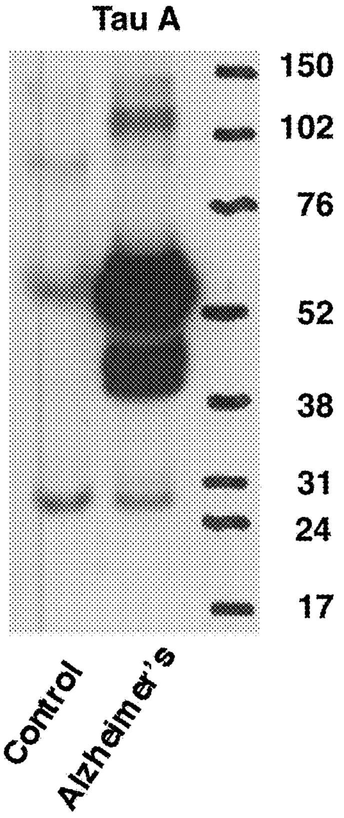

FIGS. 3A-3B show Western blots comparing brain extracts from wt and Tg4510 mice. FIG. 3A) a western blot conducted with an antibody recognizing intact Tau (MAB3420 Chemicon). FIG. 3B) Western blot conducted with in house antibody (NB191).

Figure 4:
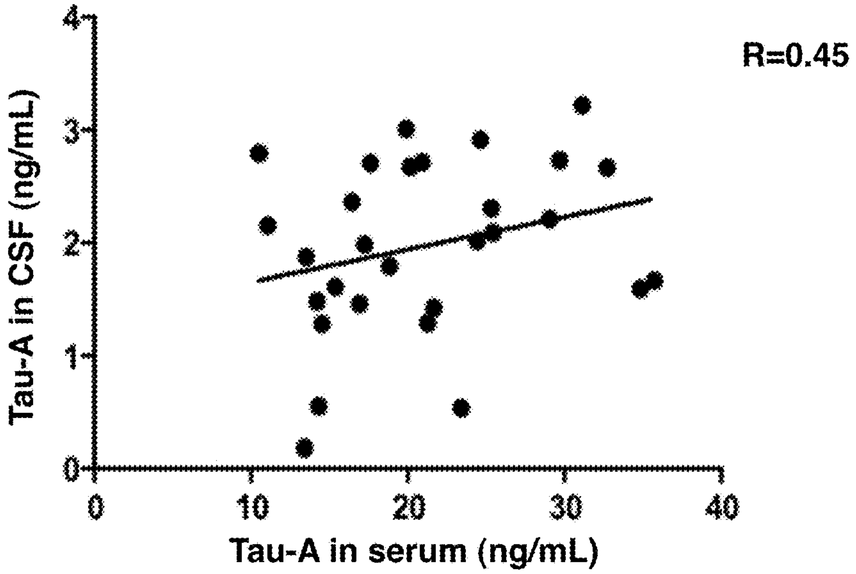

FIG. 4 shows correlation of the levels of the ADAM10 generated Tau fragment in CSF and serum samples, showing that it can be monitored in both samples.

Figure 5A:
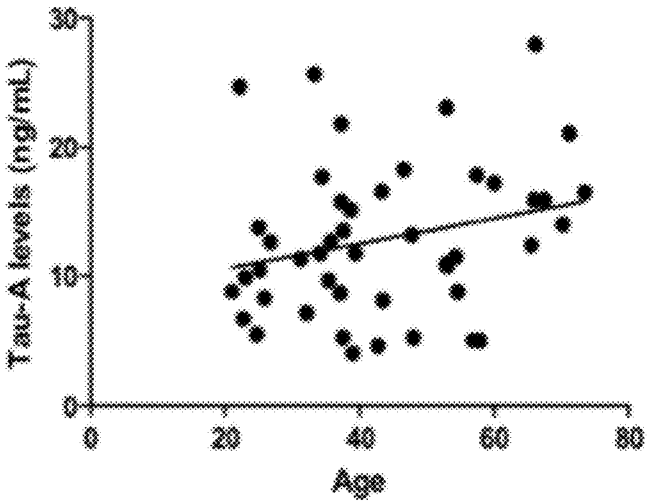
Figure 5B:
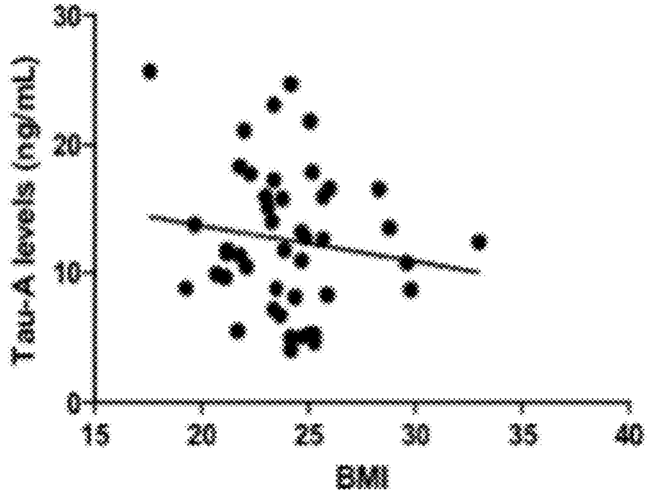

FIGS. 5A-5B show correlation of the Tau fragment to age, but not BMI.

Figure 6:
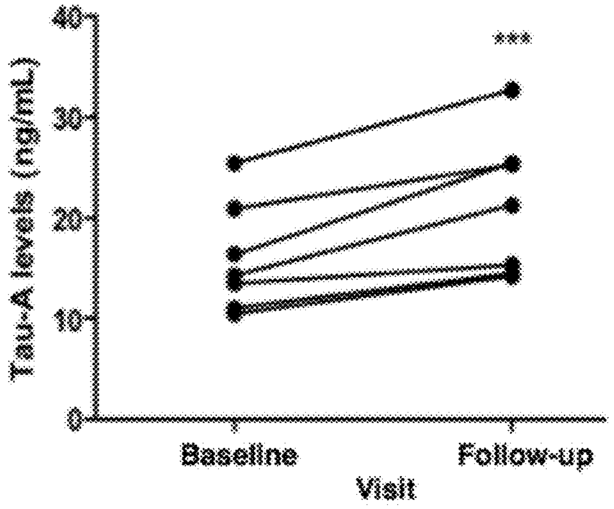

FIG. 6 shows the ability of the Tau fragment level to follow progression of severe Alzheimer's in women.

Figure 7A:
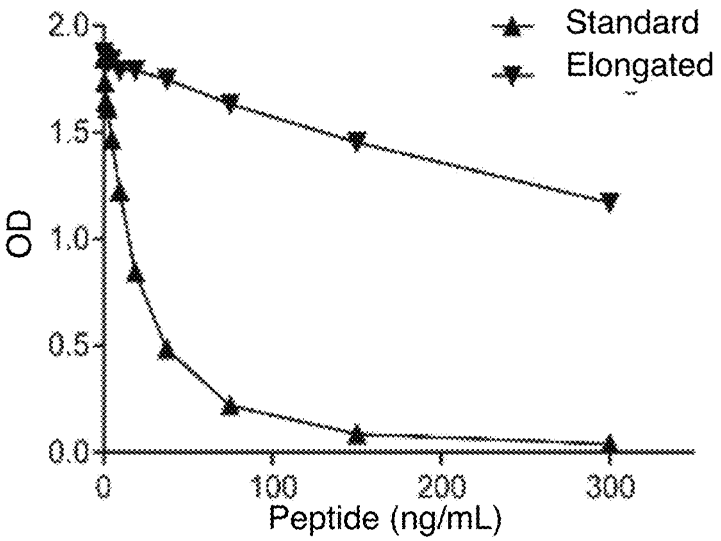
Figure 7B:
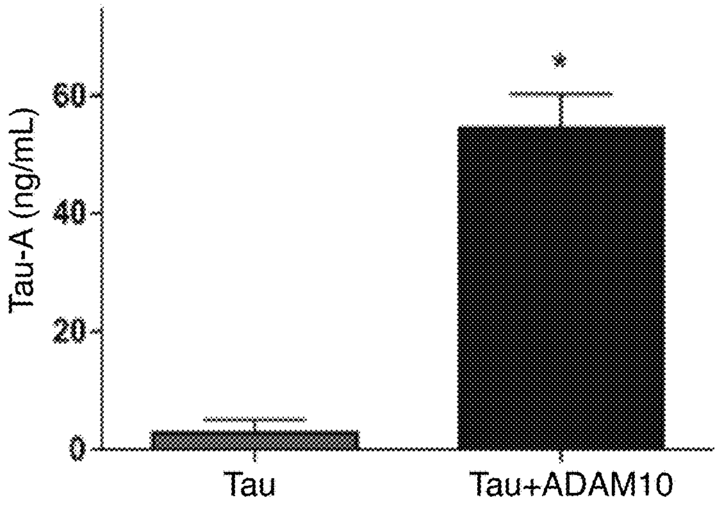
Figure 7C:
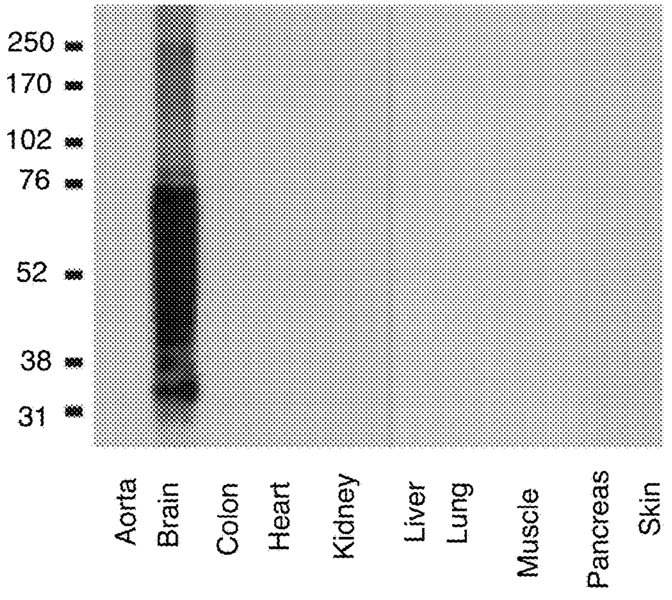
Figure 7D:
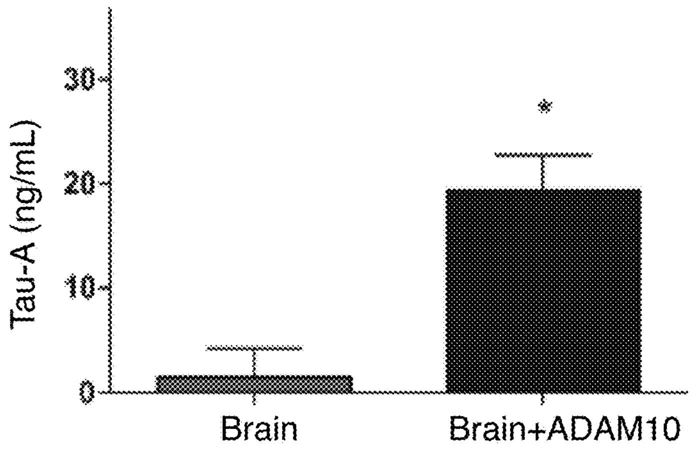
Figure 7E:
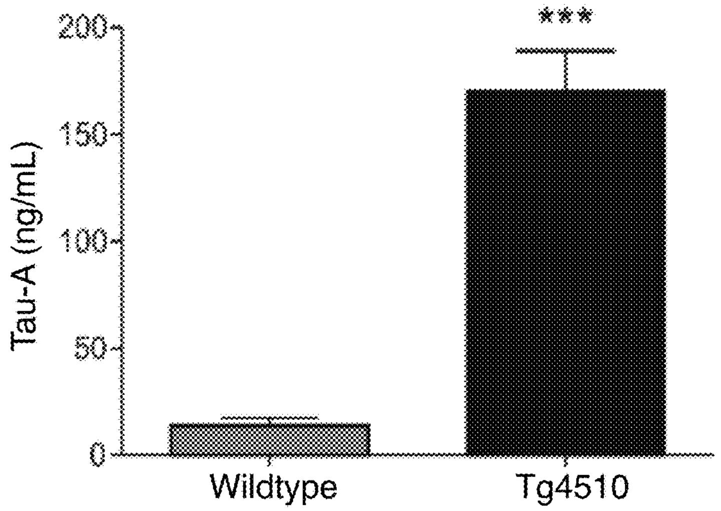
Figure 7F:
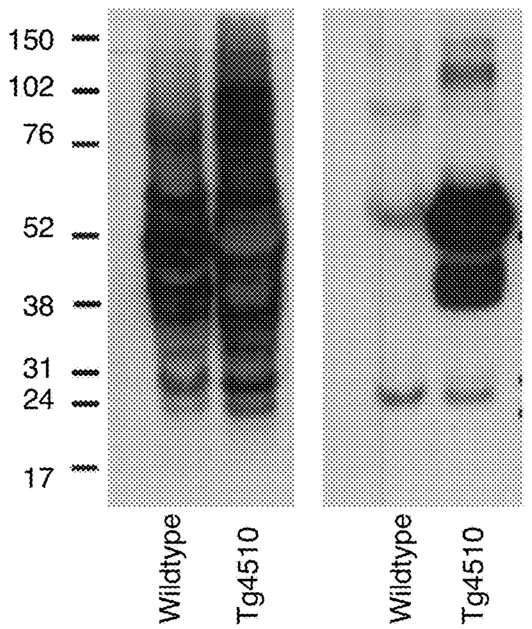

FIGS. 7A-7F show results from Example 2 characterising and providing biological validation of the Tau-A assay. FIG. 7A) Standard curves with either the selection peptide or the elongated peptide at concentrations of 0, 0.59, 1.17, 2.34, 4.69, 9.38, 18.75, 37.5, 75, 150, and 300 ng/ml. FIG. 7B) Measurement of Tau-A fragments in in vitro digests of Tau. FIG. 7C) Western blots of extracted tissues, FIG. 7D) ELISA measurement of brain extracts in the presence or absence of ADAM10. FIG. 7E) Tau-A levels in extracted brains from either control or Tg4510mice (a model of Alzheimer's disease) measured using the ELISA. FIG. 7F) Western blots comparing brain extracts from wild type and Tg4510 mice. Left: a western blot conducted with an antibody recognizing intact Tau (MAB3420 Chemicon). Right: Western blot conducted with in-house antibody (NB191).

Figure 8:
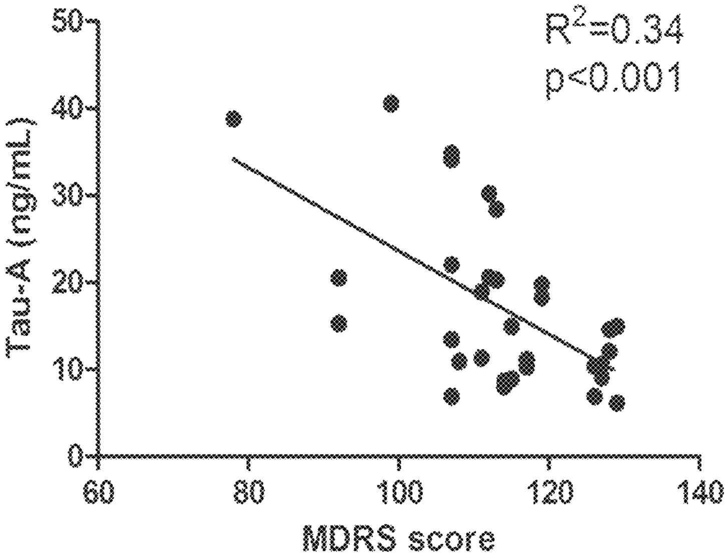

FIG. 8 shows pathology related changes in Tau-A levels demonstrating an inverse correlation between Tau-A and the Mattis Dementia Rating Scale (MDRS).

The following examples further explain and illustrate the invention.

EXAMPLE 1

In Vitro Cleavage

Recombinant TAU was cleaved either with activated ADAM10 or BACE1. Protease cleavage was performed by mixing 100 μg and 1 μg of enzyme (ADAM10 or BACE1) in secretase buffer (100 mM NaAcetate, pH 4.0) for 3 days. Finally the cleavage was verified by visualization using the SilverXpress® Silver Staining Kit (cat. no. LC6100, Invitrogen, Carlsbad, Calif., USA) according to the manufacturer's instructions.

Peptide Identification

Peptide fragments in the in vitro cleaved samples were identified using matrix-assisted laser desorption time of flight mass spectrometry (MALDI-TOF MS) and liquid chromatography coupled to electro spray ionization (ESI) tandem mass spectrometry (LC-MS/MS). MALDI-TOF samples were purified using C18 zip-tips (cat. no. ZTC18SO24, Millipore, Billerica, Mass., USA) according to specifications and 0.1 μg of material was eluted onto a MTP 384 ground steel target plate (Bruker-Daltonics, Bremen, Germany). MALDI tandem mass spectra were recorded on a Bruker ultraflex MALDI-TOF/TOF mass spectrometer (Bruker-Daltonics, Bremen, Germany) in positive ion reflector mode. Mass spectra were externally calibrated in the m/z range of 800-4000 using peptides generated by tryptic digestion of bovine β-lactoglobulin. The m/z software "Flexanalysis" (Bruker-Daltonics, Bremen, Germany) was used to analyze spectra. LCMS samples were ultra-filtrated to remove proteins above 10 kDa, the pH was adjusted to 2.0 using formic acid, and a 4 μL sample was analyzed by LC-MS/MS. LC was performed on a nanoACQUITY UPLC BEH C18 column (Waters, Milford, Mass., USA) using a formic acid/acetonitrile gradient. MS and MS/MS were performed on a Synapt High Definition Mass Spectrometry quadruple time of flight MS (QUAD-TOF; Waters, Milford, Mass., USA), with acquisition range of 350-1600 m/z in MS and 50-2000 m/z, in MS/MS. The software "ProteinLynx Global SERVER (PLGS)" (Waters, Milford, Mass., USA) was used to analyze spectra and generate peak lists. To identify peptides, MS and MS/MS data was searched against Tau (FASTA) protein database using the Mascot 2.2 (Matrix Science, Boston, Mass., USA) software with either the MALDI-TOF/TOF or ESI-QUAD-TOF settings.

The following peptide fragments were identified:

M indicates an oxidized methionine

```
Tau + BACE 1
Peptide
                                     SEQ ID NO 46
LAKQGL

                                     SEQ ID NO 91
SLAKQGL

                                      SEQ ID NO 6
ASLAKQGL

                                     SEQ ID NO 25
EVSASLAK
```

-continued

| | |
|---|---|
| SASLAKQGL | SEQ ID NO 87 |
| VSASLAKQGL | SEQ ID NO 135 |
| SPGSPGTPGSRS | SEQ ID NO 93 |
| EVSASLAKQGL | SEQ ID NO 26 |
| HVPGGGNKKIE | SEQ ID NO 34 |
| EVMEDHAGTYG | SEQ ID NO 21 |
| RKDQGGYTMHQD | SEQ ID NO 78 |
| NIHHKPGGGQVEVK | SEQ ID NO 58 |
| TLADEVSASLAKQGL | SEQ ID NO 116 |
| ATLADEVSASLAKQGL | SEQ ID NO 7 |
| TSPRHLSNVSSTGSID | SEQ ID NO 131 |
| LATLADEVSASLAKQGL | SEQ ID NO 47 |
| EAAGHVTQARMVSKSKD | SEQ ID NO 15 |
| QLATLADEVSASLAKQGL | SEQ ID NO 68 |
| EVMEDHAGTYGLGDRKD | SEQ ID NO 22 |
| EVMEDHAGTYGLGDRKD | SEQ ID NO 23 |
| SPQLATLADEVSASLAKQGL | SEQ ID NO 101 |
| RKDQGGYTMHQDQEGDTD | SEQ ID NO 79 |
| MVDSPQLATLADEVSASLAKQGL | SEQ ID NO 55 |
| TSPRHLSNVSSTGSIDMVDSPQL | SEQ ID NO 132 |
| TPSLEDEAAGHVTQARMVSKSKD | SEQ ID NO 129 |
| EAAGHVTQARMVSKSKDGTGSDDKKAKGAD | SEQ ID NO 16 |
| EVMEDHAGTYGLGDRKDQGGYTMHQDQEGD | SEQ ID NO 24 |
| LKNVKSKIGSTENLKHQPGGGKVQIINKKLD | SEQ ID NO 48 |
| HGAEIVYKSPVVSGDTSPRHLSNVSSTGSIDMVDSPQL | SEQ ID NO 32 |
| TSPRHLSNVSSTGSIDMVDSPQLATLADEVSASLAKQGL | SEQ ID NO 133 |
| LKNVKSKIGSTENLKHQPGGGKVQIINKKLDLSNVQSK | SEQ ID NO 49 |

-continued

| Tau + ADAM 10 Peptide | |
|---|---|
| TPPAPK | SEQ ID NO 117 |
| ATRIPA | SEQ ID NO 8 |
| QARMVS | SEQ ID NO 67 |
| STENLK | SEQ ID NO 110 |
| SPRHLS | SEQ ID NO 102 |
| PMPDLK | SEQ ID NO 60 |
| SEKLDF | SEQ ID NO 88 |
| LPTPPTR | SEQ ID NO 50 |
| DEAAGHVT | SEQ ID NO 13 |
| HVPGGGSVQ | SEQ ID NO 36 |
| APVPMPDL | SEQ ID NO 3 |
| SPGTPGSRS | SEQ ID NO 99 |
| EDHAGTYG | SEQ ID NO 17 |
| PVPMPDLK | SEQ ID NO 65 |
| EGDTDAGLK | SEQ ID NO 18 |
| PVPMPDLK | SEQ ID NO 66 |
| SPSSAKSRL | SEQ ID NO 103 |
| TAPVPMPDL | SEQ ID NO 111 |
| APVPMPDLK | SEQ ID NO 4 |
| APVPMPDLK | SEQ ID NO 5 |
| VPGGGNKKIE | SEQ ID NO 134 |
| SPGSPGTPGSR | SEQ ID NO 92 |
| TPPKSPSSAK | SEQ ID NO 121 |
| IPAKTPPAPK | SEQ ID NO 37 |
| RTPPKSPSSA | SEQ ID NO 80 |
| AAPPGQKGQAN | SEQ ID NO 1 |

-continued

SEQ ID NO 14
DRKDQGGYT

SEQ ID NO 89
SGDTSPRHLS

SEQ ID NO 104
SPSSAKSRLQ

SEQ ID NO 83
RTPSLPTPPT

SEQ ID NO 69
QTAPVPMPDL

SEQ ID NO 112
TAPVPMPDLK

SEQ ID NO 126
TPRGAAPPGQK

SEQ ID NO 113
TAPVPMPDLK

SEQ ID NO 93
SPGSPGTPGSRS

SEQ ID NO 27
GAAPPGQKGQAN

SEQ ID NO 26
EVSASLAKQGL

SEQ ID NO 63
PPTREPKKVA

SEQ ID NO 34
HVPGGGNKKIE

SEQ ID NO 33
HKPGGGQVEVK

SEQ ID NO 62
PPKSGDRSGYS

SEQ ID NO 107
SRTPSLPTPPT

SEQ ID NO 73
RIPAKTPPAPK

SEQ ID NO 114
TAPVPMPDLKN

SEQ ID NO 70
QTAPVPMPDLK

SEQ ID NO 2
AAPPGQKGQANAT

SEQ ID NO 71
QTAPVPMPDLK

SEQ ID NO 84
RTPSLPTPPTR

SEQ ID NO 35
HVPGGGNKKIET

SEQ ID NO 94
SPGSPGTPGSRSR

SEQ ID NO 28
GAAPPGQKGQANAT

SEQ ID NO 57
NIHHKPGGGQVE

SEQ ID NO 29
GEPPKSGDRSGYS

-continued

SEQ ID NO 95
SPGSPGTPGSRSRT

SEQ ID NO 9
ATRIPAKTPPAPK

SEQ ID NO 122
TPPKSPSSAKSRL

SEQ ID NO 115
TAPVPMPDLKNVK

SEQ ID NO 124
TPPSSGEPPKSGDR

SEQ ID NO 90
SGEPPKSGDRSGYS

SEQ ID NO 51
LPTPPTREPKKVA

SEQ ID NO 105
SPVVSGDTSPRHLS

SEQ ID NO 59
PGSPGTPGSRSRTPS

SEQ ID NO 127
TPRGAAPPGQKGQAN

SEQ ID NO 40
KAKTDHGAEIVYK

SEQ ID NO 123
TPPKSPSSAKSRLQ

SEQ ID NO 58
NIHHKPGGGQVEVK

SEQ ID NO 81
RTPPKSPSSAKSRL

SEQ ID NO 96
SPGSPGTPGSRSRTPS

SEQ ID NO 53
MHQDQEGDTDAGLK

SEQ ID NO 106
SRSRTPSLPTPPTR

SEQ ID NO 74
RIPAKTPPAPKTPPS

SEQ ID NO 54
MHQDQEGDTDAGLK

SEQ ID NO 42
KSPVVSGDTSPRHLS

SEQ ID NO 7
ATLADEVSASLAKQGL

SEQ ID NO 85
RTPSLPTPPTREPK

SEQ ID NO 118
TPPAPKTPPSSGEPPK

SEQ ID NO 64
PSSGEPPKSGDRSGYS

SEQ ID NO 128
TPRGAAPPGQKGQANAT

SEQ ID NO 52
LPTPPTREPKKVAVV

SEQ ID NO 82
RTPPKSPSSAKSRLQ

-continued

| | |
|---|---|
| ENAKAKTDHGAEIVY | SEQ ID NO 19 |
| SRTPSLPTPPTREPK | SEQ ID NO 108 |
| KTPPAPKTPPSSGEPPK | SEQ ID NO 43 |
| ENAKAKTDHGAEIVYK | SEQ ID NO 20 |
| TPPSSGEPPKSGDRSGYS | SEQ ID NO 125 |
| GTPGSRSRTPSLPTPPTR | SEQ ID NO 31 |
| RTPSLPTPPTREPKKVA | SEQ ID NO 86 |
| RENAKAKTDHGAEIVYK | SEQ ID NO 72 |
| GSPGTPGSRSRTPSLPTPPT | SEQ ID NO 30 |
| SRTPSLPTPPTREPKKVA | SEQ ID NO 109 |
| TPPAPKTPPSSGEPPKSGDR | SEQ ID NO 119 |
| KTPPAPKTPPSSGEPPKSGDR | SEQ ID NO 44 |
| SPGSPGTPGSRSRTPSLPTPPT | SEQ ID NO 97 |
| RIPAKTPPAPKTPPSSGEPPK | SEQ ID NO 75 |
| SPGSPGTPGSRSRTPSLPTPPTR | SEQ ID NO 98 |
| PPAPKTPPSSGEPPKSGDRSGYS | SEQ ID NO 61 |
| KSKDGTGSDDKKAKGADGKTKIA | SEQ ID NO 41 |
| ATRIPAKTPPAPKTPPSSGEPPK | SEQ ID NO 10 |
| TPPAPKTPPSSGEPPKSGDRSGYS | SEQ ID NO 120 |
| IPAKTPPAPKTPPSSGEPPKSGDR | SEQ ID NO 38 |
| KTPPAPKTPPSSGEPPKSGDRSGYS | SEQ ID NO 45 |
| RIPAKTPPAPKTPPSSGEPPKSGDR | SEQ ID NO 76 |
| SPGTPGSRSRTPSLPTPPTREPKKVA | SEQ ID NO 100 |
| ATRIPAKTPPAPKTPPSSGEPPKSGDR | SEQ ID NO 11 |
| IPAKTPPAPKTPPSSGEPPKSGDRSGYS | SEQ ID NO 39 |
| RIPAKTPPAPKTPPSSGEPPKSGDRSGYS | SEQ ID NO 77 |
| TRIPAKTPPAPKTPPSSGEPPKSGDRSGYS | SEQ ID NO 130 |

-continued

| | |
|---|---|
| ATRIPAKTPPAPKTPPSSGEPPKSGDRSGYS | SEQ ID NO 12 |
| NATRIPAKTPPAPKTPPSSGEPPKSGDRSGYS | SEQ ID NO 56 |

Selection of Peptide for Immunizations

The first six amino acids of each free end of the sequences identified by MS were regarded as neo-epitopes generated by the protease in question. All obtained protease-generated sequences were analyzed for homology and distance to other cleavage sites and then blasted for homology using the NPS@: network protein sequence analysis.

Reagents and Peptides

All reagents were standard high-quality chemicals from companies such as Merck and Sigma Aldrich. The synthetic peptides used for monoclonal antibody production and validation were: (a) immunogenic peptide: TPRGAAPPGQ-GGC-KLH (SEQ ID NO 248-KLH) (Keyhole-Limpet-Hemocyanin), (b) screening peptide TPRGAAPPGQ (SEQ ID NO 246), (c) de-selection peptide ATPRGAAPPGQ (SEQ ID NO 247) which has been elongated with one amino acid in the N-terminus were purchased from Chinese Peptide Company, Beijing, China. Peptide conjugation reagents were produced by Pierce (Thermofisher, Denmark).

Buffers Used for the ELISAs

Buffer used for dissolving the coating peptide was composed of the following: (150 mM Trizma, 1% BSA, 0.05% Tween-20, 0.36% Bronidox L5, pH 8.0 (Tris-BTB), and reaction stopping buffer composed of 0.1% $H_2SO_4$.

ELISA-plates used for the assay development were Streptavidin-coated from Roche cat.: 11940279. All ELISA plates were analysed with the ELISA reader from Molecular Devices, SpectraMax M, (CA, USA).

Development of an ELISA

Methods for monoclonal antibody development are previously described ([6]. Briefly, 4-6-week-old Balb/C mice were immunized subcutaneously with 200 μl emulsified antigen and 50 μg TPRGAAPPGQ-GGC-KLH (SEQ ID NO 248-KLH). Consecutive immunizations were performed at 2-week intervals in Freund's incomplete adjuvant, until stable sera titre levels were reached, and the mice were bled from the 2nd immunization on. At each bleeding, the serum titre was detected and the mouse with highest antiserum titre was selected for fusion. The selected mouse was rested for 1 month followed by intravenous boosting with 50 ng TPRGAAPPGQ-GGC-KLH (SEQ ID NO 248-KLH) in 100 μl 0.9% Sodium Chloride solution 3 days before isolation of the spleen for cell fusion.

Fusion

The fusion procedure previously described [16] was followed with SP2/0 as myeloma cells. The fusion cells were cloned in 35-mm cell culture dishes by the semi-solid medium method and the dishes were incubated in a $CO_2$-incubator. Next, clones were plated into sixteen 96-well microtiter plates and left for three days, followed by screening of culture supernatants.

Antibody Screening

Supernatants were screened in a competitive ELISA setting. Peptide TPRGAAPPGQ (SEQ ID NO 246) was used as the selection peptide and the ATPRGAAPPGQ (SEQ ID NO 247) as the elongated peptide. Cell lines specific to selection peptide and without cross-reactivity to the elongated peptide were selected and the antibodies were purified.

Tau-A ELISA Methodology

In preliminary experiments, we optimized the reagents, their concentrations and the incubation periods by performing several checkerboard analyses. The Tau-A ELISA was developed as follows: A 96-well ELISA plate pre-coated with streptavidin was further coated with 6 ng/ml of the synthetic peptide TPRGAAPPGQ-Biotin (SEQ ID NO 246-Biotin) dissolved in Tris-BTB buffer at 20° C. for 30 min by constant shaking at 300 rpm. The plate was washed five times in washing buffer and 20 µl of sample was added, followed by 100 µl of peroxidase conjugated anti-human mAb-Tau-A solution (50 ng/ml). The plate was incubated for 1 h at 20° C. in 100 mM Tris-BTB buffer during which time it was shaken at 300 rpm.

The plate was again washed five times followed by addition of 100 µl tetramethylbenzinidine (TMB) (Kem-En-Tec cat. 438OH). The plate was incubated for 15 min in darkness and shaken at 300 rpm. In order to cease the reaction, 100 µl of stopping solution (95-97% H2SO4, Merck Cat. No.: 1.00731) was added and the plate was analysed in the ELISA reader at 450 nm with 650 nm as the reference.

Standards

A standard curve was performed by serial dilution of TPRGAAPPGQ-biotin (SEQ ID NO 246-biotin). Standard concentrations were 0, 0.782, 1.5625, 3.125, 6.25, 12.5, 25, 50, and 100 ng/ml.

Samples for Testing Native Reactivity of the Antibodies

During assay development and validation serum from healthy adult subjects of different age and gender were used. Serum samples are obtained from young healthy volunteers 23-45 years of age. We also tested serum samples from different species including mouse and rat to determine the level of interspecies cross reactivity. Finally, we also tested cerebrospinal Fluid (CSF) and plasma samples.

Animal Samples

Flash frozen brains from 5 wildtype and 5 Tg4510 Tauopathy mice aged 5 months [9] were extracted according to the following protocol:

The tissue was pulverized using a Bessman pulverizer and weighed. The tissue was extracted using 250 mg tissue/mL extraction buffer (50 mM Tris-HCl, 50 mM HEPES, 15% glycerol, 1 mM EDTA, 0.5% sodium deoxycholate, Roche protease inhibitor (cat#05 056 489001), final pH8.3). The lysate was cleared by sonication, and the supernatants were collected after centrifugation at 4° C./5 min/10000 rpm. Protein concentration was determined using the DC Protein Assay from BioRad.

Western Blotting

100 µg of each extract was loaded onto an SDS-PAGE gel. The gel was run and the samples were transferred to nitrocellulose membranes as described by [23]. The levels of Tau-A fragments and total Tau protein were detected by incubation with the primary antibodies diluted to 100 ng/mL in TBS-T containing skim milk powder [22]. A secondary antibody recognizing mouse IgG conjugated to horse-radish peroxidase was then used, and finally the blot was visualized using enhanced chemiluminescence as previously described [21].

Human Samples

Two sets of human samples were used. One set (51 samples) was a collection of serum samples from an osteoarthritis study, this study contained participants with ages from 18-75, as well as Body Mass Index data [7].

The second set of samples was paired serum and CSF samples from patients with severe Alzheimer's disease. These samples contained a subset of samples collected within the same individuals at baseline and follow-up (18 months later).

Statistical Analysis

For assay validation, optical density was fitted against analyte concentration applying a four-parameter logistic regression to the calibration curve. Average, standard deviations, percentage coefficient of variation (% CV), and differences from theoretical values were calculated for all standards and samples. Quantitative data were analysed using GraphPad Prism 5 (GraphPad Software, San Diego, Calif., USA). Significant differences between means were determined using the Student's two-tailed unpaired t-test, not assuming Gaussian distribution. Correlations between serum Tau values and the rest of the variables studied were analysed using Linear Regression. Data was expressed as mean±standard error of the mean and differences were considered significant at a p level of 0.05 or lower.

Results

ELISA Technical Specifications

The antibody with best native reactivity, affinity and stability in the assay was chosen from the antibody-producing clones generated after the fusion of spleen- and myeloma cells. The clone chosen for antibody purification and the subsequent development of the ELISA was NB191-3C4, raised against TPRGAAPPGQ (SEQ ID NO 246).

Standard Curve and Recovery

Figure 1:
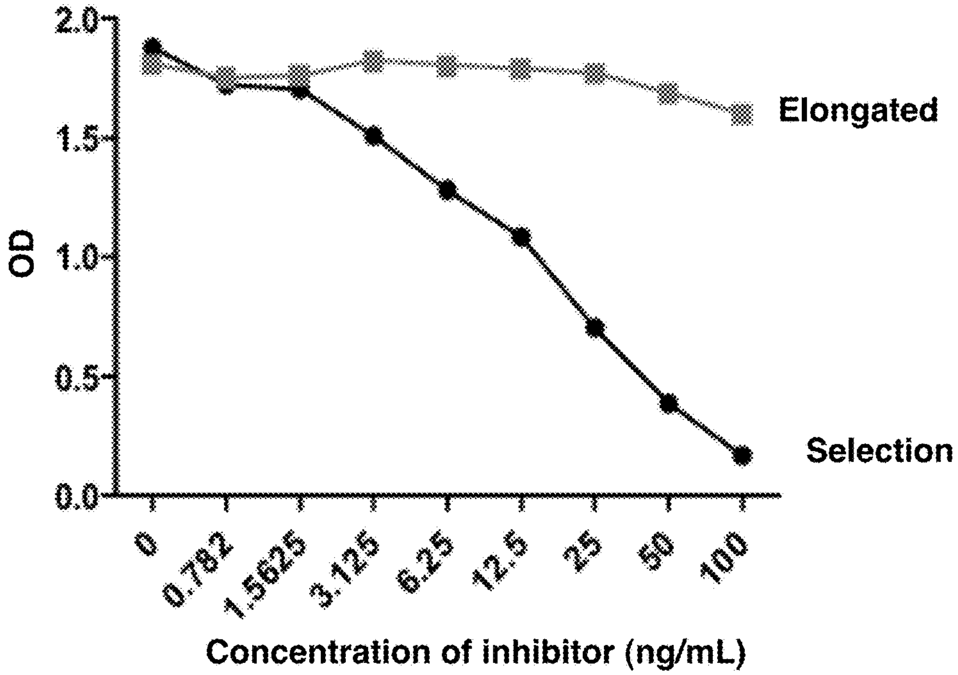
FIG. 1 shows and example of a standard curve with either the selection peptide or the elongated peptide at concentrations of 0, 0.782, 1.5625, 3.125, 6.25, 12.5, 25, 50, and 100 ng/mL.

A typical standard curve is presented in FIG. 1, showing chosen standards and the 4-parametric fit equation for determination of sample concentration, based on peptide concentrations of 0, 0.782, 1.5625, 3.125, 6.25, 12.5, 25, 50, and 100 ng/mL. In addition the specificity of the antibody is shown by comparison to the same concentrations of the elongated peptide giving no reaction at all.

Determination of the linearity or recovery by dilution in different samples resulted in following. The average determined recoveries back-calculated from samples diluted 1+1, 1+2, 1+3, 1+4, 1+5, 1+6 and 1+7 to undiluted sample were close to 100% and within the recommended ±10% (data not shown).

Separation of Brains from Alzheimer's Mice and their Controls

Figure 2:
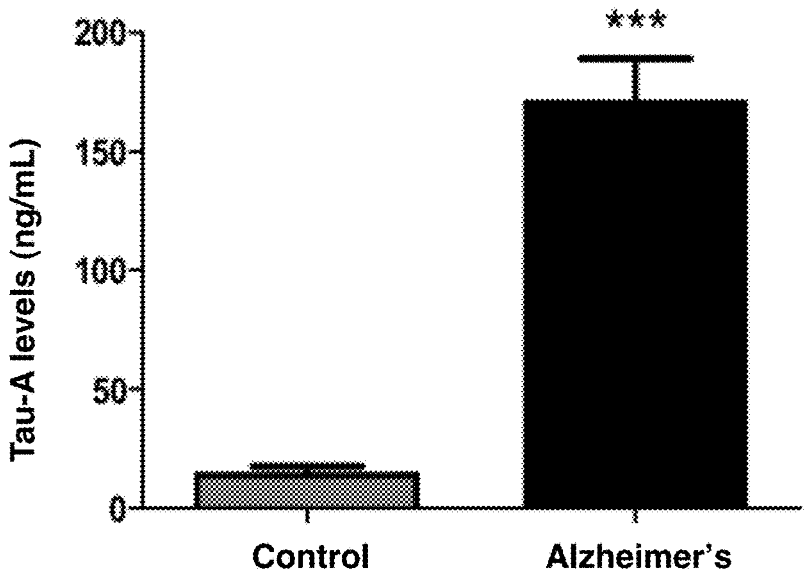
FIG. 2 shows competitive ELISA test results measured in extracted brains from either control or Tg4510 mice (a model of Alzheimer's disease).

The extracted brains from the Tg4510 mice and their corresponding controls were evaluated by measuring them in the NB191-3C4 ELISA setup. As seen in FIG. 2, a very clear separation was seen, with the Tg4510 showing 10-fold higher levels of Tau-A, when compared to the corresponding controls. In addition, a western blot was performed, and as seen in FIGS. 3A-3B the Tg4510 mice showed very high levels of Tau-A, while the control mice showed very little, even if equal amounts of protein were loaded (data not shown). On the other re-probing the blot with an antibody against total Tau showed almost equal levels of total Tau, although the intensity of the high molecular weight bands was higher in the Tg4510 correlating with Tau aggregation in this pathology.

Correlation of CSF and Serum Levels of Tau-A

In 33 paired samples of CSF and serum we investigated whether there was a correlation between Tau-A levels in the two analytes. As seen in FIG. 4 useful levels of Tau-A were detected in both analytes, and a modest, albeit not significant, correlation was observed.

Tau-A Correlates to Age, but not Body Mass Index

In the serum samples from the OA study, we performed an evaluation of Tau-A levels as a function of age and body mass index. Here we found a trend towards a positive correlation with age (FIG. 5A), but no correlation with BMI (FIG. 5B). These data indicate that Tau-A increases with age as a marker of Alzheimer's should.

Indication of Disease Progression

A subset of the serum samples from the Alzheimer's cohort was samples collected at baseline and 18 months later. Although these data only are from women, FIG. 6 shows a strong indication that in these 7 women, the levels of Tau-A increase from baseline to follow-up, hence indicating that Tau-A increases with increasing disease, as it is well-known that development of Alzheimer's is a continuous process.

EXAMPLE 2

Samples for Testing Native Reactivity of the Antibodies

For assay development and validation, serum and plasma from 15 healthy adult volunteers aged 23-45 years and of both genders were used. We also tested serum samples from mice and rats to determine the level of interspecies cross reactivity.

Animal Samples

Tissues including brain, liver, muscle, colon, kidney, lung, skin and pancreas isolated from 5 six-month-old Sprague Dawley rats and 5 brains from each of either the wildtype or Tg4510 mice were flash-frozen in liquid nitrogen and pulverized using a Bessman pulverizer. The "powder" was transferred to a vial and weighed. Extraction buffer (50 mM Tris-HCl, 50 mM HEPES, 1 mM EDTA, 0.5% sodium deoxycholate, 15% glycerol, protease inhibitor cocktail (Roche cat#05056489001), pH8.3) was added at 1 mL buffer/250 mg tissue. The lysate was cleared by sonication. After sonication the debris was spun at 4° C./5 min/10000 rpm and the supernatants were collected and stored at −80° C. until further use. Protein concentrations were determined using the DC Protein Assay (Biorad).

In Vitro Cleavage of Tissues

Protease cleavage was performed by mixing 100 μg of tissue extract and 1 μg of ADAM10 in MMP buffer (100 mM Tris-HCl, 100 mM NaCl, 10 mM $CaCl_2$, 2 mM Zn acetate, pH 8.0) and incubating for 7 days. Finally, the cleavage was verified by western blotting and ELISA analysis.

Western Blotting

20 μg of each rat tissue extract and 100 μg of each mouse tissue extract was loaded onto an SDS-PAGE gel. The gel was run and the samples were transferred to nitrocellulose membranes as previously described [15]. Ponceau Red staining was then used to verify equal protein loading on the membranes. The levels of Tau-A fragments and total Tau protein were detected by incubation with the primary antibodies diluted to 100 ng/mL in TBS-T containing skim milk powder [15]. A secondary antibody recognizing mouse IgG conjugated to horse-radish peroxidase was then added, and finally the blot was visualized using enhanced chemiluminescence as previously described [15].

Human Samples

Serum samples from Alzheimer's patients (n=21) were obtained. Characteristics: Age at onset 70(+/−7), Females/Males (16/6), baseline MDRS score 112(+/−12), Intact tau levels 849 (+/−1009).

Characterization of the Tau-A ELISA Assay

An antibody recognizing the ADAM10 generated cleavage sequence of Tau (TPRGAAPPGQ, SEQ ID NO 246) was selected and used for development of an ELISA (Tau-A). As seen in FIG. 7A, the assay was specific for the cleavage site, as extension of the sequence by one amino acid led to loss of reactivity. Further validation of specificity using ADAM10 degraded recombinant tau or brain extracts confirmed the specificity towards cleaved tau (FIG. 7B-C). In addition, tissue profiling confirmed that Tau primarily originates from the brain. The lower limit of detection (LLOD) was determined to be 2.9 ng/mL and the upper limit of detection (ULOD) was 226.3 ng/mL. The assay was technically robust and was able to detect Tau-A levels in human serum and plasma, as well as mouse and rat serum within dilution ranges of 1+2 to 1+6 (data not shown). In addition, a linear spiking recovery was obtained within the above described dilution ranges (data not shown). The intra-assay coefficient of variation was 5.8%, while the inter-assay CV % was 12.6%. No loss of reactivity was observed following 5 consecutive freeze-thaw cycles.

Biological Validation of the Tau-A ELISA

Analysis using the ELISA revealed that Tg4510 mice brains had 10-fold higher levels of Tau-A than their corresponding wt. controls (FIG. 7E). Western blotting also showed that Tg4510 mice had very high levels of Tau-A, while the control mice had very little (FIG. 7F). Re-probing the blot with an antibody against total Tau showed almost equal levels of total Tau, although the intensity of the high molecular weight bands was greater in the Tg4510.

Tau-A Levels Correlate with MDRS Score

To investigate whether a relationship between the marker and AD disease stage could be identified, we correlated the Tau-A levels in the AD patients to scores obtained using the Mattis Dementia Rating Scale [10], and found a significant (p=0.003) and inverse relationship between MDRS and Tau-A (FIG. 8). No correlations to other parameters, such as intact Tau in CSF or age could be observed in this cohort (data not shown).

Discussion

Potential serum and/or plasma-based markers for AD have been investigated extensively, yet a single biomarker with a correlation to cognitive function previously remained to be identified [1-3]. This, to our knowledge, is the first biochemical marker monitoring proteolytic processing of Tau in serum, which appears to be a key initiator of AD pathology [9]. It is also the first single serum biomarker of a brain specific protein which correlates to cognitive function. While neo-epitopes have been extensively investigated in AD, as measurements of Aβ42 and phosphorylated Tau have been reported as neo-epitopes formed as a consequence of disease [4], selective screening of serum for in vitro generated Tau fragments had not previously been undertaken.

The combination of ADAM10 and Tau selected for this work was based on the novel hypothesis that during progression of AD, Tau will be exposed to secretase-mediated cleavage either directly in the brain or as fragments generated by other brain proteases, which then become secondarily processed as they enter the circulation; however, this requires further studies. We were able to detect a specific ADAM10-generated Tau peptide fragment in serum, as well as highly elevated levels in the brains of the Tg4510 mice. These observations suggest ADAM10 processing of Tau is a relevant process in neuronal death during AD, although the exact mechanism of action still remains to be identified.

In summary, we have developed the first serum-based assay detecting pathological fragments of Tau. This fragment was directly and inversely related to cognitive function. The assay provides a useful and practical tool for the diagnosis of neuronal loss, and can be used to monitor the efficacy of treatments and progression of AD.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCE LIST

1. Alzheimer's Disease Clinical Trials. 2010. US National Institutes of Health & http://www.clinicaltrials.gov/ct2/results?term=alzheimer. Ref Type: Generic
2. Understanding stages and symptoms of Alzheimer's disease. 2010. www.nia.nih.gov/Alzheimers/Publications/stages.htm. Ref Type: Generic
3. World Alzheimer Report 2009. 2010. Alzheimer's Disease International. Ref Type: Generic
4. Arai T, Guo J P, McGeer P L (2005) Proteolysis of non-phosphorylated and phosphorylated tau by thrombin. J. Biol. Chem. 280:5145-5153
5. Arriagada P V, Growdon J H, Hedley-Whyte E T, Hyman B T (1992) Neurofibrillary tangles but not senile plaques parallel duration and severity of Alzheimer's disease. Neurology 42:631-639
6. Barascuk N, Veidal S S, Larsen L, Larsen D V, Larsen M R, Wang J, Zheng Q, Xing R, Cao Y, Rasmussen L M, Karsdal M A (2010) A novel assay for extracellular matrix remodeling associated with liver fibrosis: An enzyme-linked immunosorbent assay (ELISA) for a MMP-9 proteolytically revealed neo-epitope of type III collagen. Clin. Biochem. 43:899-904
7. Bay-Jensen A C, Liu Q, Byrjalsen I, Li Y, Wang J, Pedersen C, Leeming D J, Dam E B, Zheng Q, Qvist P, Karsdal M A (2011) Enzyme-linked immunosorbent assay (ELISAs) for metalloproteinase derived type II collagen neoepitope, CIIM—increased serum CIIM in subjects with severe radiographic osteoarthritis. Clin. Biochem. 44:423-429
8. Cummings J L (2011) Biomarkers in Alzheimer's disease drug development. Alzheimers. Dement. 7:e13-e44
9. de C A, Spires-Jones T L, Pitstick R, Carlson G A, Hyman B T (2009) Tangle-bearing neurons survive despite disruption of membrane integrity in a mouse model of tauopathy. J. Neuropathol. Exp. Neurol. 68:757-761
10. De S B (2010) Proteases and proteolysis in Alzheimer disease: a multifactorial view on the disease process. Physiol Rev. 90:465-494
11. De S B, Annaert W (2000) Proteolytic processing and cell biological functions of the amyloid precursor protein. J. Cell Sci. 113 (Pt 11):1857-1870
12. Fillit H, Leveugle B (1995) Disorders of the extracellular matrix and the pathogenesis of senile dementia of the Alzheimer's type. Lab Invest 72:249-253
13. Forstl H, Kurz A (1999) Clinical features of Alzheimer's disease. Eur. Arch. Psychiatry Clin. Neurosci. 249:288-290
14. Gamblin T C, Chen F, Zambrano A, Abraha A, Lagalwar S, Guillozet A L, Lu M, Fu Y, Garcia-Sierra F, LaPointe N, Miller R, Berry R W, Binder L I, Cryns V L (2003) Caspase cleavage of tau: linking amyloid and neurofibrillary tangles in Alzheimer's disease. Proc. Natl. Acad. Sci. U.S.A 100:10032-10037
15. Garcia-Sierra F, Mondragon-Rodriguez S, Basurto-Islas G (2008) Truncation of tau protein and its pathological significance in Alzheimer's disease. J. Alzheimers. Dis. 14:401-409
16. Gefter M L, Margulies D H, Scharff M D (1977) A simple method for polyethylene glycol-promoted hybridization of mouse myeloma cells. Somatic. Cell Genet. 3:231-236
17. Goedert M, Spillantini M G, Jakes R, Rutherford D, Crowther R A (1989) Multiple isoforms of human microtubule-associated protein tau: sequences and localization in neurofibrillary tangles of Alzheimer's disease. Neuron 3:519-526
18. Gomez-Isla T, Hollister R, West H, Mui S, Growdon J H, Petersen R C, Parisi J E, Hyman B T (1997) Neuronal loss correlates with but exceeds neurofibrillary tangles in Alzheimer's disease. Ann. Neurol. 41:17-24
19. Haass C, Selkoe D J (2007) Soluble protein oligomers in neurodegeneration: lessons from the Alzheimer's amyloid beta-peptide. Nat. Rev. Mol. Cell Biol. 8:101-112
20. Hanger D P, Wray S (2010) Tau cleavage and tau aggregation in neurodegenerative disease. Biochem. Soc. Trans. 38:1016-1020
21. Henriksen K, Gram J, Schaller S, Dahl B H, Dziegiel M H, Bollerslev J, Karsdal M A (2004) Characterization of osteoclasts from patients harboring a G215R mutation in C1C-7 causing autosomal dominant osteopetrosis type II. Am J Pathol 164:1537-1545
22. Henriksen K, Gram J, Schaller S, Dahl B H, Dziegiel M H, Bollerslev J, Karsdal M A (2004) Characterization of osteoclasts from patients harboring a G215R mutation in ClC-7 causing autosomal dominant osteopetrosis type II. Am J Pathol 164:1537-1545
23. Henriksen K, Gram J, Schaller S, Dahl B H, Dziegiel M H, Bollerslev J, Karsdal M A (2004) Characterization of osteoclasts from patients harboring a G215R mutation in C1C-7 causing autosomal dominant osteopetrosis type II. Am J Pathol 164:1537-1545
24. Hoglund K, Hansson O, Buchhave P, Zetterberg H, Lewczuk P, Londos E, Blennow K, Minthon L, Wiltfang J (2008) Prediction of Alzheimer's disease using a cerebrospinal fluid pattern of C-terminally truncated beta-amyloid peptides. Neurodegener. Dis. 5:268-276
25. Jin S, Agerman K, Kolmodin K, Gustafsson E, Dahlqvist C, Jureus A, Liu G, Falting J, Berg S, Lundkvist J, Lendahl U (2010) Evidence for dimeric BACE-mediated APP processing. Biochem. Biophys. Res. Commun. 393:21-27
26. Kim B, Backus C, Oh S, Hayes J M, Feldman E L (2009) Increased tau phosphorylation and cleavage in mouse models of type 1 and type 2 diabetes. Endocrinology 150:5294-5301
27. McKhann G, Drachman D, Folstein M, Katzman R, Price D, Stadlan E M (1984) Clinical diagnosis of Alzheimer's disease: report of the NINCDS-ADRDA Work Group under the auspices of Department of Health and Human Services Task Force on Alzheimer's Disease. Neurology 34:939-944
28. Molsa P K, Marttila R J, Rinne U K (1986) Survival and cause of death in Alzheimer's disease and multi-infarct dementia. Acta Neurol. Scand. 74:103-107
29. Park S Y, Tournell C, Sinjoanu R C, Ferreira A (2007) Caspase-3- and calpain-mediated tau cleavage are differentially prevented by estrogen and testosterone in beta-amyloid-treated hippocampal neurons. Neuroscience 144:119-127
30. Polyikoski T, Sulkava R, Haltia M, Kainulainen K, Vuorio A, Verkkoniemi A, Niinisto L, Halonen P, Kontula K (1995) Apolipoprotein E, dementia, and cortical deposition of beta-amyloid protein. N. Engl. J. Med. 333:1242-1247

31. Rametti A, Esclaire F, Yardin C, Terro F (2004) Linking alterations in tau phosphorylation and cleavage during neuronal apoptosis. J. Biol. Chem. 279:54518-54528
32. Reifert J, Hartung-Cranston D, Feinstein S C (2011) Amyloid {beta}-Mediated Cell Death of Cultured Hippocampal Neurons Reveals Extensive Tau Fragmentation without Increased Full-length Tau Phosphorylation. J. Biol. Chem. 286:20797-20811
33. Schroeter M L, Stein T, Maslowski N, Neumann J (2009) Neural correlates of Alzheimer's disease and mild cognitive impairment: a systematic and quantitative meta-analysis involving 1351 patients. Neuroimage. 47:1196-1206
34. Takeda S, Sato N, Rakugi H, Morishita R (2010) Plasma beta-amyloid as potential biomarker of Alzheimer disease: possibility of diagnostic tool for Alzheimer disease. Mol. Biosyst.
35. Vassar R, Kandalepas P C (2011) The beta-secretase enzyme BACE1 as a therapeutic target for Alzheimer's disease. Alzheimers. Res. Ther. 3:20
36. Vincent B, Checker F (2011) alpha-Secretase in Alzheimer's Disease and Beyond: Mechanistic, Regulation and Function in the Shedding of Membrane Proteins. Curr. Alzheimer Res.
37. Waldemar G, Dubois B, Emre M, Georges J, McKeith I G, Rossor M, Scheltens P, Tariska P, Winblad B (2007) Recommendations for the diagnosis and management of Alzheimer's disease and other disorders associated with dementia: EFNS guideline. Eur. J. Neurol. 14:e1-26
38. Zetterberg H (2008) Biomarkers reflecting different facets of Alzheimer's disease. Eur. J. Neurol. 15:1143-1144
39. Zetterberg H, Andreasson U, Hansson O, Wu G, Sankaranarayanan S, Andersson M E, Buchhave P, Londos E, Umek R M, Minthon L, Simon A J, Blennow K (2008) Elevated cerebrospinal fluid BACE1 activity in incipient Alzheimer disease. Arch. Neurol. 65:1102-1107
40. Zhang S, Salemi J, Hou H, Zhu Y, Mori T, Giunta B, Obregon D, Tan J (2010) Rapamycin promotes beta-amyloid production via ADAM-10 inhibition. Biochem. Biophys. Res. Commun.

The invention claimed is:

1. A method of detecting fragments of Tau protein formed by secretase cleavage of Tau protein in a human patient, said method comprising:

a. obtaining a sample from the human patient; and b. detecting whether said fragments of Tau are present in the sample by contacting the sample with an antibody and detecting binding between the fragments and the antibody wherein said antibody is raised against a synthetic peptide corresponding to a C-terminal or N-terminal neo-epitope amino acid sequence formed by cleavage of Tau protein by a secretase and has specific binding affinity for said C-terminal or N-terminal neo-epitope amino acid sequence, and wherein said antibody has specific binding affinity for any of the following sequences at the N terminal of a peptide:

| | |
|---|---|
| APVPMP | SEQ ID NO 137 |
| APVP**M**P | SEQ ID NO 138 |
| ASLAKQ | SEQ ID NO 139 |
| ATLADE | SEQ ID NO 140 |
| ATRIPA | SEQ ID NO 8 |
| DEAAGH | SEQ ID NO 141 |
| DRKDQG | SEQ ID NO 142 |
| EAAGHV | SEQ ID NO 143 |
| EDHAGT | SEQ ID NO 144 |
| EGDTDA | SEQ ID NO 145 |
| EVMEDH | SEQ ID NO 147 |
| EVMEDH | SEQ ID NO 148 |
| EVSASL | SEQ ID NO 149 |
| GAAPPG | SEQ ID NO 150 |
| GEPPKS | SEQ ID NO 151 |
| GSPGTP | SEQ ID NO 152 |
| GTPGSR | SEQ ID NO 153 |
| HGAEIV | SEQ ID NO 154 |
| HKPGGG | SEQ ID NO 155 |
| IPAKTP | SEQ ID NO 156 |
| KAKTDH | SEQ ID NO 157 |
| KSPVVS | SEQ ID NO 159 |
| KTPPAP | SEQ ID NO 160 |
| LAKQGL | SEQ ID NO 46 |
| LATLAD | SEQ ID NO 161 |
| LKNVKS | SEQ ID NO 162 |
| LPTPPT | SEQ ID NO 163 |
| MHQDQE | SEQ ID NO 164 |
| **M**HQDQE | SEQ ID NO 165 |

-continued

| | |
|---|---|
| MVDSPQ | SEQ ID NO 166 |
| NATRIP | SEQ ID NO 167 |
| NIHHKP | SEQ ID NO 168 |
| PMPDLK | SEQ ID NO 60 |
| PPAPKT | SEQ ID NO 170 |
| PPKSGD | SEQ ID NO 171 |
| PPTREP | SEQ ID NO 172 |
| PVPMPD | SEQ ID NO 173 |
| PVP**M**PD | SEQ ID NO 174 |
| QARMVS | SEQ ID NO 67 |
| QLATLA | SEQ ID NO 175 |
| QTAPVP | SEQ ID NO 176 |
| RENAKA | SEQ ID NO 177 |
| RIPAKT | SEQ ID NO 178 |
| RKDQGG | SEQ ID NO 179 |
| RTPSLP | SEQ ID NO 181 |
| SASLAK | SEQ ID NO 182 |
| SEKLDF | SEQ ID NO 88 |
| SGDTSP | SEQ ID NO 183 |
| SGEPPK | SEQ ID NO 184 |
| SLAKQG | SEQ ID NO 185 |
| SPGSPG | SEQ ID NO 186 |
| SPRHLS | SEQ ID NO 102 |
| SPSSAK | SEQ ID NO 188 |
| SPVVSG | SEQ ID NO 189 |
| SRSRTP | SEQ ID NO 190 |
| SRTPSL | SEQ ID NO 191 |
| STENLK | SEQ ID NO 110 |
| TAPVPM | SEQ ID NO 192 |
| TAPVP**M** | SEQ ID NO 193 |
| TLADEV | SEQ ID NO 194 |
| TPPAPK | SEQ ID NO 117 |
| TPPKSP | SEQ ID NO 195 |
| TPPSSG | SEQ ID NO 196 |
| TPRGAA | SEQ ID NO 197 |
| TPSLED | SEQ ID NO 198 |
| TRIPAK | SEQ ID NO 199 |
| TSPRHL | SEQ ID NO 200 |
| VPGGGN | SEQ ID NO 201 |
| VSASLA | SEQ ID NO 202 |

where M indicates an oxidised methionine or wherein said antibody has specific binding affinity for any of the following sequences at the C terminal of a peptide:

| | |
|---|---|
| AAGHVT | SEQ ID NO 203 |
| AEIVYK | SEQ ID NO 204 |
| AKSRLQ | SEQ ID NO 205 |
| APPGQK | SEQ ID NO 206 |
| ATRIPA | SEQ ID NO 8 |
| DLKNVK | SEQ ID NO 207 |
| DQGGYT | SEQ ID NO 208 |
| DRSGYS | SEQ ID NO 209 |
| EPKKVA | SEQ ID NO 210 |
| GAEIVY | SEQ ID NO 211 |
| GGGQVE | SEQ ID NO 212 |
| GGGSVQ | SEQ ID NO 213 |
| GKTKIA | SEQ ID NO 214 |
| GNKKIE | SEQ ID NO 215 |
| GQANAT | SEQ ID NO 216 |
| GQVEVK | SEQ ID NO 217 |
| GSRSRT | SEQ ID NO 218 |
| GTPGSR | SEQ ID NO 153 |
| HAGTYG | SEQ ID NO 219 |
| INKKLD | SEQ ID NO 220 |
| KAKGAD | SEQ ID NO 221 |
| KSPSSA | SEQ ID NO 223 |
| LAKQGL | SEQ ID NO 46 |
| LGDRKD | SEQ ID NO 224 |
| LPTPPT | SEQ ID NO 163 |
| MPDLKN | SEQ ID NO 225 |
| NKKIET | SEQ ID NO 226 |
| PGSRSR | SEQ ID NO 227 |
| PKSGDR | SEQ ID NO 228 |
| PKTPPS | SEQ ID NO 229 |
| PMPDLK | SEQ ID NO 60 |
| P**M**PDLK | SEQ ID NO 230 |
| PTREPK | SEQ ID NO 232 |

-continued

| | |
|---|---|
| QDQEGD | SEQ ID NO 233 |
| QEGDTD | SEQ ID NO 234 |
| QKGQAN | SEQ ID NO 235 |
| RSRTPS | SEQ ID NO 236 |
| SAKSRL | SEQ ID NO 237 |
| SASLAK | SEQ ID NO 182 |
| SEKLDF | SEQ ID NO 88 |
| SGEPPK | SEQ ID NO 184 |
| SNVQSK | SEQ ID NO 238 |
| SPRHLS | SEQ ID NO 102 |
| SPSSAK | SEQ ID NO 188 |
| STENLK | SEQ ID NO 110 |
| STGSID | SEQ ID NO 239 |
| TPGSRS | SEQ ID NO 241 |
| TPPAPK | SEQ ID NO 117 |
| VDSPQL | SEQ ID NO 242 |
| VPMPDL | SEQ ID NO 243 |
| VSKSKD | SEQ ID NO 244 |
| YTMHQD | SEQ ID NO 245 |

where M indicates an oxidised methionine.

2. The method of claim 1, wherein the neo-epitope is formed by cleavage of a Tau protein by ADAM10 or BASE-1.

3. The method of claim 1, wherein said antibody has specific binding affinity for the following sequence at the N terminal of a peptide: TPRGAAPPGQ (SEQ ID NO 246).

4. The method of claim 1, wherein said antibody is a monoclonal antibody or a fragment of a monoclonal antibody having specific binding affinity.

5. The method of claim 1, wherein said method is conducted as a competition immunoassay in which said antibody and a competition agent are incubated in the presence of said sample and the competition agent competes with the peptide fragments in the sample to bind to the antibody.

6. The method of claim 5, wherein said competition agent is a synthetic peptide or is a purified native peptide formed by cleavage of the protein from which said epitope comes so as to reveal said neo-epitope.

7. The method of claim 6, wherein said competition agent comprises a peptide comprising the N-terminal sequence TPRGAAPPGQ (SEQ ID NO 246).

8. The method of claim 1, wherein the sample is a sample of urine, serum, blood, plasma, or saliva.

* * * * *